(12) United States Patent
Giordano et al.

(10) Patent No.: US 6,630,589 B1
(45) Date of Patent: Oct. 7, 2003

(54) IDENTIFICATION OF COMPOUNDS FOR THE TREATMENT OR PREVENTION OF PROLIFERATIVE DISEASES

(75) Inventors: Anthony Giordano, Phoenixville, PA (US); Gordon Donald Powers, Malvern, PA (US); Michael Alan Sturgess, Perkasie, PA (US); Ke Yang, Boothwyn, PA (US)

(73) Assignee: Message Pharmaceuticals, Malvern, PA (US)

( * ) Notice: Subject to any disclaimer, the term of this patent is extended or adjusted under 35 U.S.C. 154(b) by 0 days.

(21) Appl. No.: 10/106,572

(22) Filed: Mar. 26, 2002

Related U.S. Application Data

(60) Provisional application No. 60/278,902, filed on Mar. 26, 2001.

(51) Int. Cl.$^7$ ...................... C07D 401/02; C07D 213/02
(52) U.S. Cl. .................... 546/139; 548/566; 546/276.4; 560/21; 564/50
(58) Field of Search ................................ 546/148, 149, 546/276.4, 312, 139; 548/566; 560/21; 564/50, 336

(56) References Cited

U.S. PATENT DOCUMENTS

| | | | |
|---|---|---|---|
| 4,704,384 A | 11/1987 | Driscoll et al. | 514/183 |
| 5,696,276 A | 12/1997 | Ahn et al. | 552/298 |
| 5,712,289 A | 1/1998 | Behforouz et al. | 514/311 |
| 5,789,431 A | 8/1998 | Lee et al. | 514/394 |
| 6,030,983 A | 2/2000 | Behforouz et al. | 514/510 |
| 6,174,918 B1 | 1/2001 | Lee et al. | 514/510 |
| 6,326,369 B1 | 12/2001 | Kato et al. | 514/237.5 |

FOREIGN PATENT DOCUMENTS

| | | |
|---|---|---|
| EP | 0 519 290 A1 | 6/2002 |
| WO | WO 00/20637 | 4/2000 |
| WO | WO 01/04313 A1 | 1/2001 |

OTHER PUBLICATIONS

Kallmayer et al, Pharmazie, Vol 46, No. 5, pp. 328–331, 1991.*
Nakazumi et al, Synthesis, Vol 10, pp. 787–879, 1982.*
Shishkina et al, Ser. Knim. Nauk, Vol 5, pp. 136–142, 1982.*
Chu et al, J. Chem. Soc, Vol 9, pp. 1083–1087, 1978.*
Babich et al., "In Vitro Cytotoxicity of 1,4–Naphthoquinone Derivatives to Replicating Cells," *Toxicology Letters* 69:69–75, 1993.
Child et al., "Cell Type–Dependent and –Independent Control of HER–2/neu Translation," *The International Journal of Biochemistry & Cell Biology* 31:201–213, 1999.
Child et al., "Translational Control by an Upstream Open Reading Frame in the HER–2/neu Transcript," *The Journal of Biological Chemistry* 274:24335–24341, 1999.
Clark et al., "The Fungicidal Activity of Substituted 1,4–Naphthoquinones. Part III: Amino, Anilino and Acylamino Derivatives," *Pestic. Sci.* 16:23–32, 1985.
Di Chenna et al., "Preparation and Cytotoxicity Toward Cancer Cells of Mono(arylimino) Derivatives of β–Lapachone," *Journal of Medicinal Chemistry* 44:2486–2489, 2001.
Gibson et al. "Relationship Between DT–Diaphorase–Mediated Metabolism of a Series of Aziridinylbenzoquinones and DNA Damage and Cytotoxicity," *Molecular Pharmacology* 42:531–536, 1992.
Johannes and Sarnow, "Cap–Independent Polysomal Association of Natural mRNAs Encoding c–myc, BiP, and eIF4G Conferred by Internal Ribosome Entry Sites," *RNA* 4:1500–1513, 1998.
Juhl et al., HER–2/neu Is Rate–Limiting for Ovarian Cancer Growth, *The Journal of Biological Chemistry* 272:29482–29486, 1997.
Qing et al., "Induction of Apoptosis in Human Leukemia K–562 and Gastric Carcinoma SGC–7901 Cells by Salvicine, A Novel Anticancer Compound," *Anti–Cancer Drugs* 12:51–56, 2001.
Ryu et al., "Synthesis and Cytotoxic Activities of 6–Chloro–7–Arylamino–5,8–Isoquinolinediones," *Bioorganic and Medicinal Chemistry Letters* 9:1075–1080, 1999.
Seth et al., "Complex Post–Transcriptional Regulation of EGF–Receptor Expression by EGF and TGF–α in Human Prostate Cancer Cells," *British Journal of Cancer* 80:657–669, 1999.
Soonthornchareonnon et al., "New Cytotoxic 1–Azaanthraquinones and 3–Aminonaphthoquinone from the Stem Bark of *Goniothalamus marcanii*," *Journal of Natural Products* 62:1390–1394, 1999.
Song et al., "Naphthazarin Derivatives (VII): Antitumor Action Against ICR Mice Bearing Ascitic S–180 Cells," *Archives of Pharmacal Research* 24:190–193, 2001.

* cited by examiner

*Primary Examiner*—Zinna Northington Davis
(74) *Attorney, Agent, or Firm*—Clark & Elbing LLP; Kristina Bieker-Brady

(57) ABSTRACT

The invention features screening assays for compounds that are potentially useful for treating or preventing a proliferative disease. The assays are based on contacting a candidate compound with a cell containing a nucleic acid including a HER2 regulatory element and a reporter sequence. In addition, the invention features compounds identified by the assays of the invention. The invention further features compounds structurally related to those identified by the screening assays. Finally, the invention features methods of treating or preventing a proliferative disease using the compounds of the invention.

34 Claims, 5 Drawing Sheets

HER2 5'UTR cDNA (SEQ ID NO: 1)

ATTCCCCTCCATTGGGACCGGAGAAACCAGGGGAGCCCCCCGGGCAGCCG
CGCGCCCCTTCCCACGGGGCCCTTTACTGCGCCGCGCGCCCGGCCCCCAC
CCCTCGCAGCACCCCGCGCCCCGCGCCCTCCCAGCCGGGTCCAGCCGGAG
CCATGGGGCCGGAGCCGCAGTGAGCACC

Figure 4

HER2 3'UTR cDNA (SEQ ID NO: 2)

ACCAGAAGGCCAAGTCCGCAGAAGCCCTGATGTGTCCTCAGGGAGCAGGGA
AGGCCTGACTTCTGCTGGCATCAAGAGGTGGGAGGGCCCTCCGACCACTTCC
AGGGGAACCTGCCATGCCAGGAACCTGTCCTAAGGAACCTTCCTTCCTGCTT
GAGTTCCCAGATGGCTGGAAGGGGTCCAGCCTCGTTGGAAGAGGAACAGCAC
TGGGGAGTCTTTGTGGATTCTGAGGCCCTGCCCAATGAGACTCTAGGGTCCA
GTGGATGCCACAGCCCAGCTTGGCCCTTTCCTTCCAGATCCTGGGTACTGAAA
GCCTTAGGGAAGCTGGCCTGAGAGGGGAAGCGGCCCTAAGGGAGTGTCTAA
GAACAAAAGCGACCCATTCAGAGACTGTCCCTGAAACCTAGTACTGCCCCCC
ATGAGGAAGGAACAGCAATGGTGTCAGTATCCAGGCTTTGTACAGAGTGCTT
TTCTGTTTAGTTTTACTTTTTTGTTTGTTTTTTAAAGATGAAATAAAGAC
CCAGGGGGAG

SEQUENCE LISTING

```
<160> NUMBER OF SEQ ID NOS: 2

<210> SEQ ID NO 1
<211> LENGTH: 178
<212> TYPE: DNA
<213> ORGANISM: Homo sapiens

<400> SEQUENCE: 1 attccctcc attgggaccg gagaaaccag gggagccccc cgggcagccg cgcgcccctt      60
cccacggggc cctttactgc gccgcgcgcc cggccccac ccctcgcagc accccgcgcc     120
ccgcgccctc ccagccgggt ccagccggag ccatggggcc ggagccgcag tgagcacc      178

<210> SEQ ID NO 2
<211> LENGTH: 531
<212> TYPE: DNA
<213> ORGANISM: Homo sapiens

<400> SEQUENCE: 2
accagaaggc caagtccgca gaagccctga tgtgtcctca gggagcaggg aaggcctgac      60
ttctgctggc atcaagaggt gggagggccc tccgaccact tccaggggaa cctgccatgc     120
caggaacctg tcctaaggaa ccttccttcc tgcttgagtt cccagatggc tggaagggt      180 ccagcctcgt tggaagagga acagcactgg ggagtctttg tggattctga ggccctgccc     240
aatgagactc tagggtccag tggatgccac agcccagctt ggcccttttcc ttccagatcc     300 tgggtactga aagccttagg gaagctggcc tgagagggga agcggcccta agggagtgtc     360
```

```
taagaacaaa agcgacccat tcagagactg tccctgaaac ctagtactgc cccccatgag    420
gaaggaacag caatggtgtc agtatccagg ctttgtacag agtgcttttc tgtttagttt    480 ttacttttt tgttttgttt ttttaaagat gaaataaaga cccaggggga g              531
```

IDENTIFICATION OF COMPOUNDS FOR THE TREATMENT OR PREVENTION OF PROLIFERATIVE DISEASES

CROSS-REFERENCE TO RELATED APPLICATIONS

This application claims benefit of co-pending U.S. Provisional Application No. 60/278,902, filed Mar. 26, 2001.

BACKGROUND OF THE INVENTION

The invention relates to the fields of screening assays and compounds and methods for treating cancer and other proliferative diseases.

The regulation of protein expression can occur at a number of levels: transcriptional, post-transcriptional, or post-translational. The modulation of protein expression is often critical for the treatment of disease. To this end, one area of research has been directed at developing small molecules that regulate transcription factors. Another approach to modulating protein expression is achieved by targeting the RNA encoding the target protein using antisense technology.

Another manner in which protein expression is regulated is through modulating translation efficiency. In eukaryotes, translational regulation usually occurs at the initiation step. Therefore, cis-elements in the 5' untranslated region (UTR) are important for overall regulation of protein synthesis. There is also a growing body of evidence that supports the role of the poly(A) tail and elements in the 3' UTR in regulating initiation of translation HER2 overexpression occurs in a number of primary human tumors, including 25–30% of breast and ovarian carcinomas, and is associated with an adverse prognosis and rapid tumor growth. HER2 is regulated at both the transcriptional and post-transcriptional level. For example, it has been previously shown that HER2 mRNA is translated more efficiently in transformed cells than in primary cells. Therefore, therapeutics that decrease HER2 polypeptide levels within a cell would be valuable as drugs for the treatment of conditions such as cancer and other proliferative diseases.

In addition, there is a need for the identification of compounds that can be used to treat cancer and proliferative diseases, regardless of the mechanism of action.

SUMMARY OF THE INVENTION

The invention features screening assays for compounds that are potentially useful for treating or preventing a proliferative disease. In addition, the invention features compounds identified by the assays of the invention. The invention further features compounds structurally related to those identified by the screening assays. Finally, the invention features methods of treating or preventing a proliferative disease using the compounds of the invention.

Accordingly, in one aspect, the invention features a method of identifying a compound for treating or preventing a proliferative disease. This method includes the steps of (a) providing a cell, e.g., a mammary cell, a gastric cell, an ovarian cell, a bladder cell, a lung cell, a salivary gland cell, or a cancer cell, including a nucleic acid molecule containing a HER2 regulatory element operatively linked to a reporter coding sequence and stably integrated into a chromosome of the cell; (b) contacting the cell with a candidate compound; and (c) assaying for the effectiveness of said candidate compound for the treatment or prevention of said proliferative disease. In one embodiment, in step (a), the method further includes adding an RNA binding protein to the cell, under conditions that allow interaction between the nucleic acid molecule and the RNA binding protein. The interaction in step (a) between said nucleic acid molecule and said RNA binding protein may also be mediated by at least one polypeptide. The nucleic acid molecule including a HER2 regulatory sequence operatively linked to a reporter coding sequence may further include one or more additional regulatory elements. The HER2 regulatory element may, for example, include a HER2 5' UTR, a HER2 3' UTR, or a HER2 5' UTR and a HER2 3' UTR. The HER2 5' UTR is, for example, SEQ ID NO: 1, and the HER2 3' UTR is, for example, SEQ ID NO: 2.

In one embodiment, the assaying in step (c) is for a change in the level of translation efficiency of the reporter coding sequence relative to a cell not exposed to the candidate compound, and a modulation in the level of translation efficiency of said reporter coding sequence indicates a compound that modulates the translation efficiency of HER2. The modulation may be an increase or decrease in the level of translation efficiency of HER2. The reporter coding sequence is, for example, a luciferase, a β-galactosidase, or a green fluorescent protein reporter sequence. In one embodiment, the translation efficiency is assayed by polysomal distribution analysis, followed by detection of the level of reporter coding RNA expression. In another embodiment, the translation efficiency is assayed by detection of the level of reporter coding protein expression or activity.

In another embodiment, the assaying in step (c) is for toxicity of the candidate compound to the cell or the compounds ability to inhibit cell growth, relative to a cell not exposed to the compound. Step (c) may further include comparing the toxicity or growth inhibition of the candidate compound to the cell to the toxicity or growth inhibition of the compound to a reference cell. The toxicity or growth inhibition of a compound to a reference cell may be, for example, representative of the toxicity or growth inhibitory effect of the compound to the general cell population.

In another aspect, the invention features compounds of the formula:

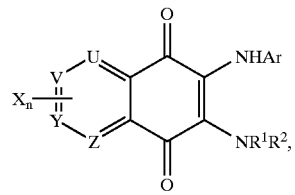

or a pharmaceutically acceptable salt thereof, wherein U, V, Y, and Z are independently C, CH, N, O, or S; X is independently H, Hal, lower alkyl, $OR^5$, $SR^6$, or $NR^7R^8$, where $R^5$, $R^6$, $R^7$, and $R^8$ are independently H or lower alkyl, and n is 1, 2, 3, or 4; $R^1$ and $R^2$ are independently H, Me, or Et, or $R^1$ and $R^2$ together are $(CR^9R^{10})_m$, where $R^9$ and $R^{10}$ are independently H, lower alkyl, $CH_2OR^{11}$, $(CH_2)_oNR^{12}R^{13}$, or $OR^{14}$, where $R^{11}$, $R^{12}$, $R^{13}$, and $R^{14}$ are H, lower alkyl, aryl, or alkaryl, m is 2, 3, 4, or 5, and o is 0 or 1; and Ar is an unsubstituted or substituted carbocyclic or heterocyclic aromatic ring or fused ring system. In one embodiment, U, V, Y, and Z are C or CH.

In another embodiment, the compound is of the formula:

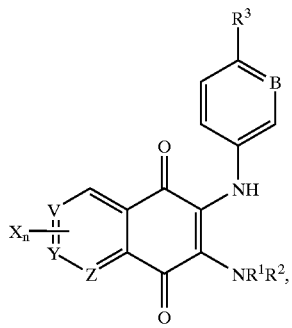

where V, Y, and Z are independently N, CH, or C; B is N, CH, or CR$^4$, where R$^4$ is F or lower alkyl; X is independently H, Hal, lower alkyl, OR$^5$, SR$^6$, or NR$^7$R$^8$, where R$^5$, R$^6$, R$^7$, and R$^8$ are independently H or lower alkyl, and n is 1, 2, 3, or 4; R$^1$ and R$^2$ are independently H, Me, or Et, or R$^1$ and R$^2$ together are (CR$^9$R$^{10}$)$_m$, where R$^9$ and R$^{10}$ are independently H, lower alkyl, CH$_2$OR$^{11}$, (CH$_2$)$_o$NR$^{12}$R$^{13}$, or OR$^{14}$, where R$^{11}$, R$^{12}$, R$^{13}$, and R$^{14}$ are independently H, lower alkyl, aryl, or alkaryl, m is 2, 3, 4, or 5, and o is 0 or 1; and R$^3$ is H, lower alkyl, F, OR$^{15}$, where R$^{15}$ is H, lower alkyl, or aralkyl, or a substituent of the structure:

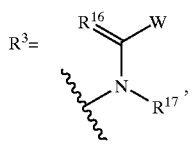

where R$^{16}$ is NH, O, or S; R$^{17}$ is H, lower alkyl, or aralkyl; and W is lower alkyl, lower alkenyl, lower alkynyl, aryl, heteroaryl, alkaryl, OR$^{18}$, or NR$^{19}$R$^{20}$, where R$^{18}$, R$^{19}$, and R$^{20}$ are independently H, lower alkyl, lower alkenyl, lower alkynyl, aryl, alkaryl, aralkyl, or (CH$_2$)$_k$CH$_2$OR$^{21}$, where R$^{21}$ is H or lower alkyl, and k is 1, 2, 3, or 4. In various embodiments, at least one of B, V, Y, and Z is N. In various other embodiments, when X$_n$ is H, V, Y, and Z are C or CH, R$^1$ and R$^2$ together are (CH$_2$)$_4$, B is CR$^4$, and R$^4$ is F, R$^3$ is not F or H; when X$_n$ is H, V, Y, and Z are C or CH, R$^1$ and R$^2$ together are (CH$_2$)$_4$, B is CR$^4$, and R$^4$ is Me, R$^3$ is not H; when X$_n$ is H, V, Y, and Z are C or CH, R$^1$ and R$^2$ together are (CH$_2$)$_4$, B is CR$^4$, and R$^4$ is H, R$^3$ is not H or F; when X$_n$ is H, V, Y, and Z are C or CH, B is CR$^4$, and R$^1$, R$^2$, and R$^4$ are Me, R$^3$ is not H; when X$_n$ is H, V, Y, and Z are C or CH, R$^1$ and R$^2$ are Me, B is CR$^4$, and R$^4$ is F, R$^3$ is not F; when X$_n$ is H, V, Y, and Z are C or CH, R$^1$ and R$^2$ together are (CH$_2$)$_4$, B is CH, W is methyl, and R$^{16}$ is O, R$^{17}$ is not H; when X$_n$ is H, V, Y, and Z are C or CH, R$^1$ and R$^2$ are methyl, B is CH, W is methyl, and R$^{16}$ is O, R$^{17}$ is not H; when X$_n$ is H, V, Y, and Z are C or CH, B is CH, and R$^1$ and R$^2$ are Me or R$^1$ and R$^2$ together are (CH$_2$)$_5$, R$^3$ is not methoxy; when X$_n$ is H, V, Y, and Z are C or CH, B is CH, and R$^1$ and R$^2$ together are (CH$_2$)$_5$, R$^3$ is not F; and X$_n$ is H, V, Y, and Z are C or CH, B is CH, and R$^1$ and R$^2$ together are (CH$_2$)$_5$, R$^3$ is not ethoxy. Exemplary compounds of the above embodiments include:

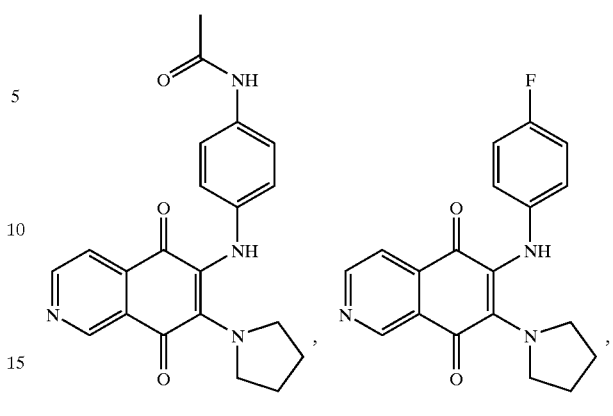

MES 10555    MES 10557

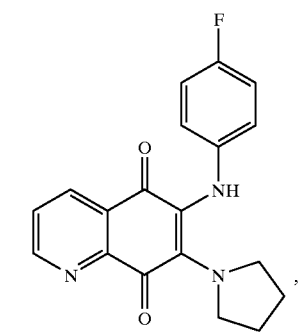

MES 10563

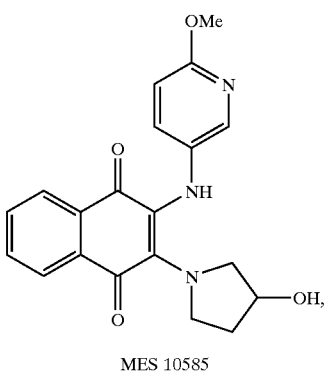

MES 10585

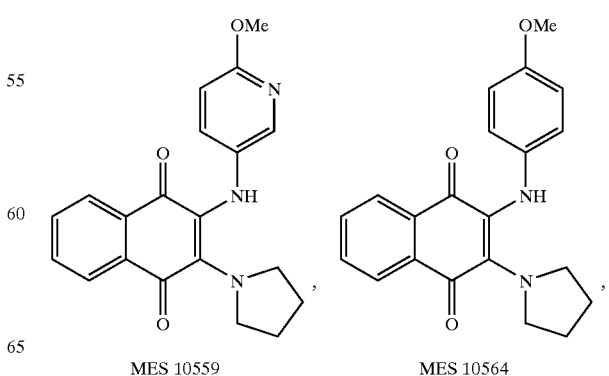

MES 10559    MES 10564

-continued

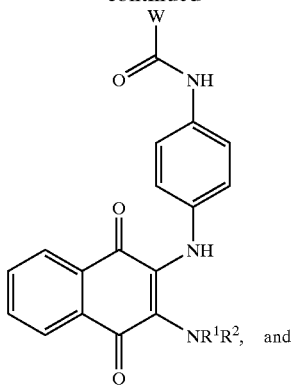

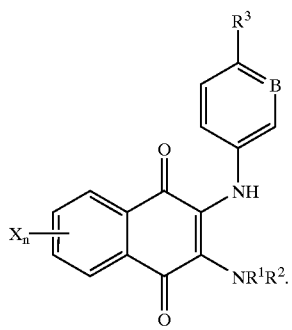

Compounds of the invention may also be of the formula:

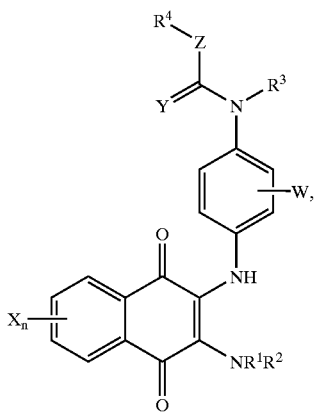

where W is H, lower alkyl, aryl, Hal, or $OR^5$, where $R^5$ is H or lower alkyl; X is independently H, Hal, lower alkyl, $OR^6$, $SR^7$, or $NR^8R^9$, where $R^6$, $R^7$, $R^8$, and $R^9$ are independently H or lower alkyl, and n is 1, 2, 3, or 4; Y is NH, O, or S; Z is O or $NR^{10}$, where $R^{10}$ is H, lower alkyl, or lower alkenyl; $R^1$ and $R^2$ are independently H, Me, or Et, or $R^1$ and $R^2$ together are $(CR^{11}R^{12})_m$, where $R^{11}$ and $R^{12}$ are independently H, lower alkyl, $CH_2OR^{13}$, $(CH_2)_oNR^{14}R^{15}$, or $OR^{16}$, where $R^{13}$, $R^{14}$, $R^{15}$, and $R^{16}$ are H, lower alkyl, aryl, or alkaryl, m is 2, 3, 4, or 5, and o is 0 or 1; $R^3$ is H or lower alkyl; and $R^4$ is H, lower alkyl, lower alkenyl, lower alkynyl, aryl, alkaryl, or $(CH_2)_kCH_2OR^{17}$, where $R^{17}$ is H or lower alkyl, and k is 1, 2, 3, or 4. In one embodiment, W is H. Exemplary compounds of these embodiments include:

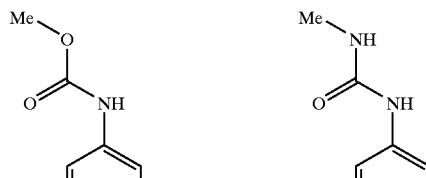

MES 13374      MES 13382

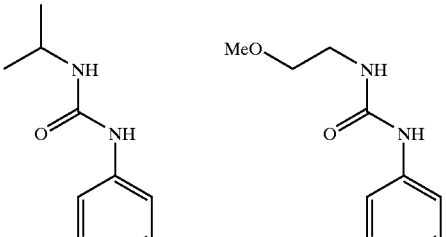

MES 13378      MES 13384

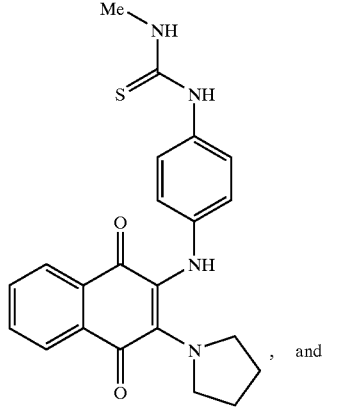

MES 10572

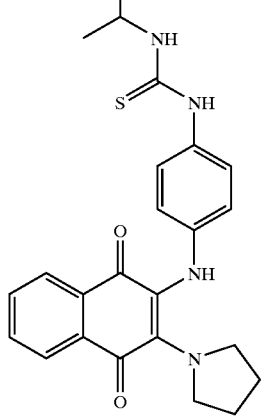

In another embodiment, the compounds are of the formula:

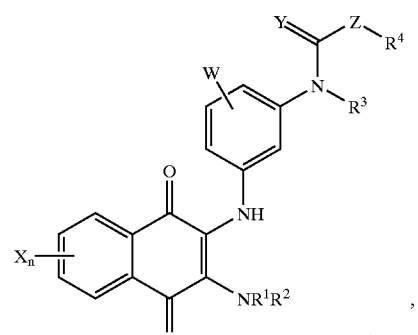

where W is H, lower alkyl, aryl, Hal, or $OR^5$, where $R^5$ is H or lower alkyl; X is independently H, Hal, lower alkyl, $OR^6$, $SR^7$, or $NR^8R^9$, where $R^6$, $R^7$, $R^8$, and $R^9$ are independently H or lower alkyl, and n is 1, 2, 3, or 4; Y is NH, O, or S; Z is O or $NR^{10}$, where $R^{10}$ is H, lower alkyl, or lower alkenyl; $R^1$ and $R^2$ are independently H, Me, or Et, or $R^1$ and $R^2$ together are $(CR^{11}R^{12})_m$, where $R^{11}$ and $R^{12}$ are independently H, lower alkyl, $CH_2OR^{13}$, $(CH_2)_oNR^{14}R^{15}$, or $OR^{16}$, where $R^{13}$, $R^{14}$, $R^{15}$, and $R^{16}$ are H, lower alkyl, aryl, or alkaryl, m is 2, 3, 4, or 5, and o is 0 or 1; $R^3$ is H or lower alkyl; and $R^4$ is H, lower alkyl, lower alkenyl, lower alkynyl, aryl, alkaryl, or $(CH_2)_kCH_2OR^{17}$, where $R^{17}$ is H or lower alkyl, and k is 1, 2, 3, or 4. An exemplary compound is:

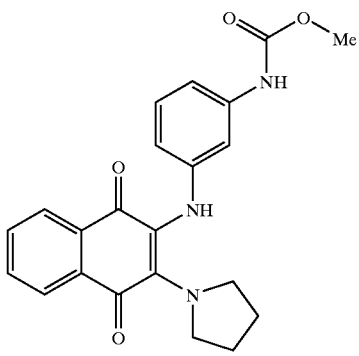

MES 13375

Compounds of the invention also include compounds of the formula:

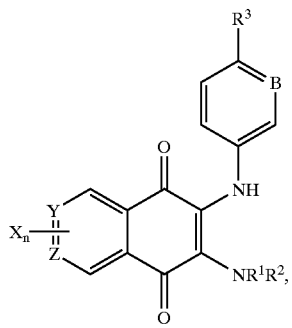

where Y and Z are independently C, CH, or N; B is N or $CR^4$, where $R^4$ is F, lower alkyl, or H; X is independently H, Hal, lower alkyl, $OR^5$, $SR^6$, or $NR^7R^8$, where $R^5$, $R^6$, $R^7$, and $R^8$ are independently H or lower alkyl, and n is 1, 2, 3, or 4; $R^1$ and $R^2$ are independently H, Me, or Et, or and $R^1$ and $R^2$ together are $(CR^9R^{10})_m$, where $R^9$ and $R^{10}$ are independently H, lower alkyl, $CH_2OR^{11}$, $(CH_2)_oNR^{12}R^{13}$, or $OR^{14}$, where $R^{11}$, $R^{12}$, $R^{13}$, $R^{14}$ are H, lower alkyl, aryl, or alkaryl, m is 2, 3, 4, or 5, and o is 0 or 1; and $R^3$ is a substituent structure of the structure:

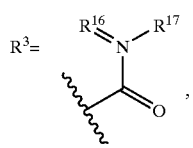

where $R^{16}$ and $R^{17}$ are independently H, lower alkyl, alkaryl, or aryl. Examples include:

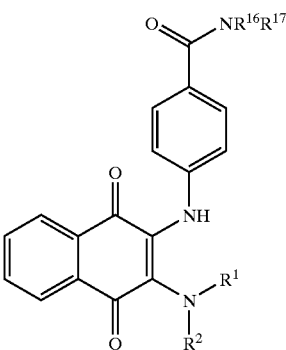

and

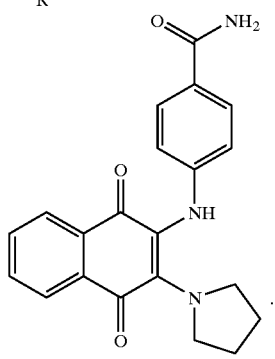

MES 10570

In another embodiment, the compounds are of the formula:

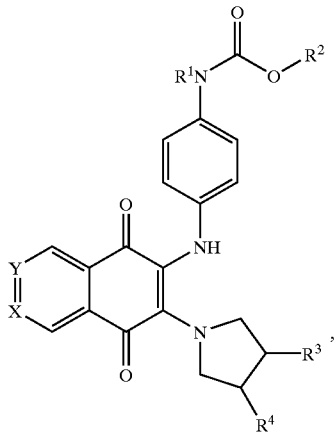

where X and Y are independently N or CH; $R^1$ is H, lower alkyl or aralkyl; $R^2$ is lower alkyl, or aralkyl; $R^3$ and $R^4$ are independently H or $OR^5$, where $R^5$ is H, lower alkyl, or $NR^6R^7$, where $R^6$ and $R^7$ are independently H or lower alkyl. Exemplary compounds of this embodiment include:

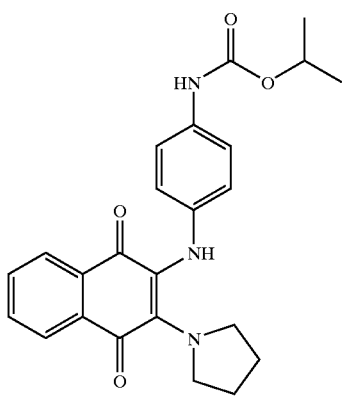

MES 13372 and

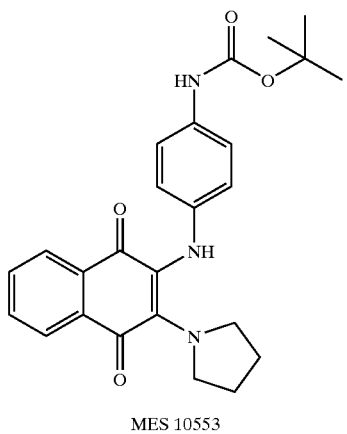

MES 10553

The invention features compounds of the formula:

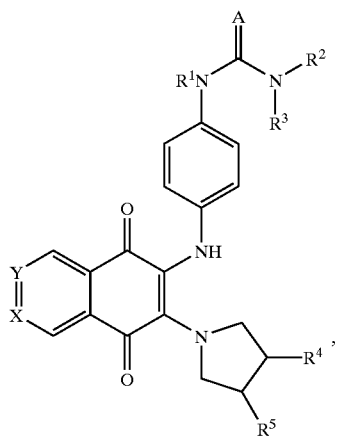

where X and Y are independently N or CH; A is O or S; $R^1$ is H, lower alkyl, or aralkyl; $R^2$ and $R^3$ are independently lower alkyl or aralkyl; and $R^4$ and $R^5$ are independently H or $OR^6$, where $R^6$ is H, lower alkyl, or $NR^7R^8$, where $R^7$ and $R^8$ are independently H or lower alkyl.

The invention also features compounds of the formula:

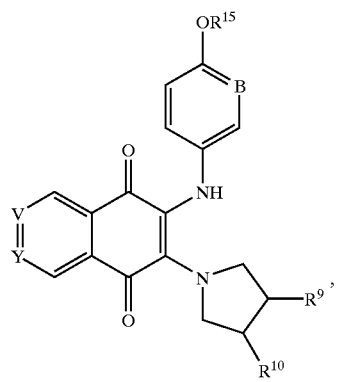

where X, Y, and Z are independently N or CH; $R^1$ is lower alkyl or aralkyl; and $R^9$ and $R^{10}$ are independently H, $OR^{14}$, where $R^{14}$ is H, lower alkyl, or $NR^{12}R^{13}$, where $R^{12}$ and $R^{13}$ are independently H or lower alkyl.

The invention further features compositions including any one or more compounds of the invention and a pharmaceutically acceptable carrier. Exemplary compounds for such compositions include:

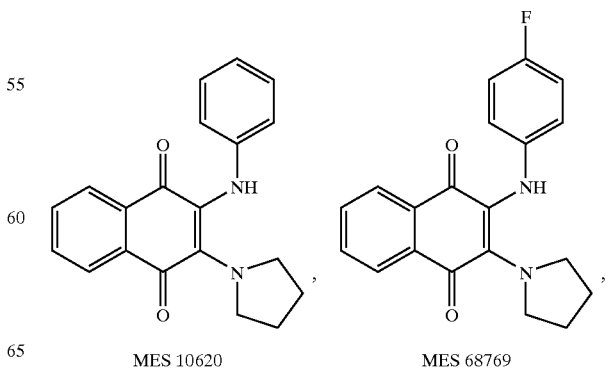

MES 10620              MES 68769

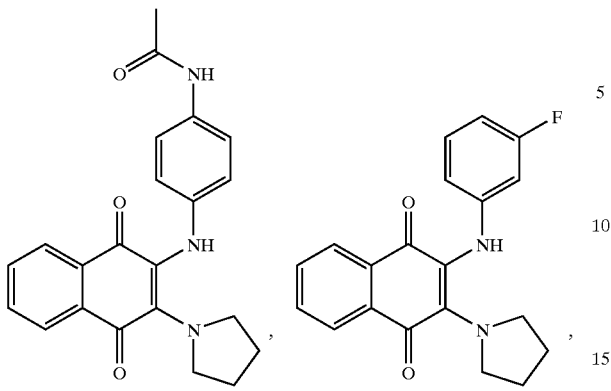

MES 51151    MES 10626

MES 68764

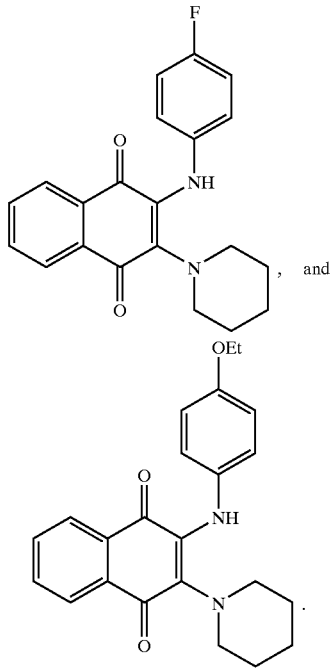

Any of the compounds of the invention may also be in the form of a pharmaceutically acceptable salt.

In another aspect, the invention features methods for treating or preventing a proliferative disease, such as cancer, in a subject, e.g., a mammal or human. The methods include administering to the subject a therapeutically effective amount of a chemical compound of the invention. The compound may be in a pharmaceutically acceptable carrier. The therapeutically effective amount is, for example, a dosage sufficient to modulate HER2 polypeptide expression.

By "alkaryl" is meant an alkyl, alkenyl, or alkynyl radical substituted with an aryl group.

By "aralkyl" is meant an aryl radical substituted with an alkyl, alkenyl, or alkynyl group.

By "aryl" is meant an aromatic carbocyclic or heterocyclic ring or fused ring system substituent. The aryl group may be substituted or unsubstituted.

By "candidate compound" or "test compound" is meant a chemical, be it naturally-occurring or artificially-derived, that is screened by employing one of the assay methods described herein. Candidate compounds may include, for example, peptides, polypeptides, synthetic organic molecules, naturally occurring organic molecules, nucleic acid molecules, sugars, polysaccharides, and derivatives thereof.

By "condition" is meant a state of being or feeling. Conditions include, but are not limited to a proliferative disease, for example, prostate cancer, breast cancer, gastrointestinal cancer, lung cancer, colon cancer, melanoma, ovarian cancer, gastric cancer, bladder cancer, salivary gland carcinoma, a brain tumor, leukemia, lymphoma, carcinoma, and the symptoms associated with cancer. Conditions also include myeloproliferative disorders.

By a "decrease" is meant a lowering in the level of translation efficiency, as measured by a lowering in the level of reporter gene expression, as assayed, for example, by polysome analysis. The decrease is, for example, at least 10%, 30%, 40%, 50%, 75%, or 90% relative to a control sample that was not administered the compound, or that was contacted with the compound vehicle only.

By a "derivative" is meant a structural derivative having a chemical modification of the compound that enhances bioavailability, solubility, or stability in vivo or ex vivo, or that reduces the toxicity to non-target cells or dosage required. Such modifications are known to those skilled in the field of medicinal chemistry.

By a "dosage sufficient to modulate HER2 polypeptide expression" is meant an amount of a chemical compound or small molecule that increases or decreases HER2 polypeptide expression when administered to a subject. For example, for a compound that decreases HER2 translation efficiency, the modulation is a decrease in HER2 polypeptide expression that is at least 10%, 30%, 40%, 50%, 75%, or 90% lower in a treated subject than in the same subject prior to the administration of the inhibitor or than in an untreated, control subject. In addition, for a compound that increases HER2 translation efficiency, the amount of HER2 polypeptide expression is, for example, at least 1.5-, 2-, 3-, 5-, 10-, or 20-fold greater in a treated subject than in the same subject prior to the administration of the modulator or than in an untreated, control subject.

By "expose" is meant to allow contact between an animal, cell, tissue, lysate or extract derived from a cell, or molecule derived from a cell, and a test compound.

By "expression vector" is meant a DNA construct that contains regulatory elements, for example, the UTR sequences of the present invention and a promoter that are operably linked to a downstream gene. Transfection of the expression vector into a recipient cell allows the cell to express RNA encoded by the expression vector. An expression vector may be a genetically engineered plasmid or virus, derived from, for example, a bacteriophage, adenovirus, retrovirus, poxvirus, herpesvirus, or artificial chromosome.

By an "increase" is meant a rise in the level of translation efficiency, as measured by a rise in reporter gene expression, as assayed, for example, by polysome analysis. The increase is, for example, at least 1.5-fold to 2-fold, by at least 3-fold to 5-fold, or by at least 10-fold to 20-fold, relative to a control sample that was not administered the compound, or that was contacted with the compound vehicle only.

By "lower alkyl," "lower alkeny", and "lower alkynyl" is meant any carbon-containing radical having between 1 and 6 carbons, e.g., between 1 and 3 carbons or between 3 and 6 carbons, and only single, one or more double, or one or more triple carbon-carbon bonds, respectively. The radical may be substituted or unsubstituted. Exemplary "lower" groups include methyl, ethyl, propyl, isopropyl, butyl, isobutyl, sec-butyl, pentyl, neopentyl, isopentyl, hexyl, 2-, 3-, or 4-methylpentyl, 2-ethylbutyl, and 2,2 or 3,3 dimethylbutyl.

By "modulates" is meant changing the level of translation efficiency, either by decrease or increase.

By "operably linked" is meant that a gene and one or more regulatory sequences are connected in such a way as to permit gene expression when the appropriate molecules (e.g., transcriptional activator proteins) are bound to the regulatory sequences. As used herein, an RNA comprising a regulatory element is operably linked to a promoter and/or 5' UTR sequences and/or 3' UTR sequences that direct transcription and/or translation of a reporter gene.

By "pharmaceutically acceptable salt" is meant a non-toxic salt of a compound of the invention formed, e.g., from non-toxic inorganic or organic acids. Such non-toxic salts include, for example, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Other pharmaceutically acceptable salts are known to those skilled in the art.

By "proliferative disease" is meant a disease that is caused by or results in inappropriately high levels of cell division, inappropriately low levels of apoptosis, or both. For example, cancers such as lymphoma, leukemia, melanoma, ovarian cancer, breast cancer, pancreatic cancer, bladder cancer, gastric cancer, salivary gland carcinoma, and lung cancer are all examples of proliferative disease. A myeloproliferative disease is another example of a proliferative disease.

By "promoter" is meant a minimal sequence sufficient to direct transcription.

By "protein" or "polypeptide" or "polypeptide fragment" is meant any chain of more than two amino acids, regardless of post-translational modification (e.g., glycosylation or phosphorylation), constituting all or part of a naturally-occurring polypeptide or peptide, or constituting a non-naturally occurring polypeptide or peptide.

By "regulatory element" is meant sequences that can modulate expression of a gene or gene product. Examples of regulatory sequences include, but are not limited to promoters, enhancers, sequences that stabilize an RNA sequence, sequences that enhance protein stability, translation termination sequences, and additional 5' or 3' UTR sequences.

By "reporter gene" or "reporter nucleic acid" is meant any gene or translatable nucleotide sequence that encodes a product whose RNA or polypeptide expression is detectable and/or quantitatable by immunological, chemical, biochemical, or biological assays. A reporter gene may be detected at the nucleic acid level by detecting nucleic acid expression, for example, by Northern blot analysis, or filter binding assays. A reporter gene product may, for example, have one of the following attributes, without restriction: fluorescence (e.g., green fluorescent protein), enzymatic activity (e.g., $\beta$-galactosidase, luciferase, chloramphenicol acetyltransferase), toxicity (e.g., ricin), or an ability to be specifically bound by a second molecule (e.g., biotin or a detectably labeled antibody). It is understood that any engineered variants of reporter genes that are readily available to one skilled in the art, are also included, without restriction, in the foregoing definition. In addition, a reporter gene is any nucleic acid sequence that is not endogenously contained as an RNA sequence of the cell of interest.

By a "substantially pure nucleic acid," "isolated nucleic acid," or "substantially pure and isolated nucleic acid" is meant DNA that is free of the genes that, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

By "therapeutically effective amount" is meant an amount of a compound sufficient to produce a preventative, healing, curative, stabilizing, or ameliorative effect in the treatment of a condition, e.g., a proliferative disease.

By "transformed cell" or "transfected cell" is meant a cell (or a descendent of a cell) into which a nucleic acid molecule has been introduced, by means of recombinant nucleic acid techniques. Such cells may be either stably or transiently transfected.

By "transformation" or "transfection" is meant any method for introducing foreign molecules into a cell (e.g., a bacterial, yeast, fungal, algal, plant, insect, or animal cell, particularly a mammalian cell). Lipofection, DEAE-dextran-mediated transfection, microinjection, protoplast fusion, calcium phosphate precipitation, retroviral delivery, electroporation, and biolistic transformation are just a few of the methods known to those skilled in the art which may be used. In addition, a foreign molecule can be introduced into a cell using a cell penetrating peptide, as described, for example, by Fawell et al. (Proc. Natl. Acad. Sci. USA 91:664–668 (1994)) and Lindgren et al. (TIPS 21:99–103 (2000)).

By "translation" is meant the process of generating a polypeptide that has an amino acid sequence dictated by the codon sequence of an mRNA that encodes the polypeptide.

By "translation efficiency" is meant the ability of an RNA to be translated into a polypeptide. Translation efficiency can be measured, for example, by polysome distribution analysis, as described herein, where an RNA with a high level of translation efficiency will be associated with high molecular weight polysomes, and an RNA with a low level of translation efficiency will not be associated with high molecular weight polysomes, or will have a smaller amount associated with high molecular weight polysomes, or will be associated with low molecular weight polysomes. Alternatively, translation efficiency can be measured by determining the level of reporter coding protein expression or activity. This may be done in combination with the detection of steady state RNA levels to confirm that a modulation in reporter polypeptide expression or activity is a result of a change in RNA translation efficiency.

In addition, translation efficiency of HER2 can be detected by determining the viability of a cell contacted with a compound that modulates HER2 translation efficiency. Reduced HER2 protein expression in tumor cells has been shown to be associated with cell toxicity (Juhl et al., J. Biol. Chem. 272:29482–29486 (1997)). Therefore, a compound that decreases the translation efficiency of HER2 will result in increased cell death, compared to control cells that are not administered the compound, or that are contacted with the compound vehicle only. Methods for assaying cell death are well known in the art. For example, cell death can be measured by determining cellular ATP levels, wherein a cell that is undergoing cell death has a decreased level of cellular ATP compared to a control cell. Cell death may also be measured by staining with a vital dye, for example, trypan blue, wherein a cell that is dying will be stained with the vital dye, and a cell that is not dying will not be stained with the dye.

The level of RNA translation efficiency in a cell contacted with a compound that decreases the level of translation efficiency may be decreased, for example, by at least 10%, 30%, 40%, 50%, 75%, or 90% relative to a control cell that was not contacted with the compound, or that was contacted with the compound vehicle only. Alternatively, the level of RNA translation efficiency in a cell contacted with a compound that increases the level of translation efficiency may be increased, for example, by at least 1.5-fold to 2-fold, by at least 3-fold to 5-fold, or by at least 10-fold to 20-fold, relative to a control sample that was not administered the compound, or that was contacted with the compound vehicle only.

By "treating" is meant the medical management of a subject, e.g. an animal or human, with the intent that a prevention, cure, stabilization, or amelioration of the symptoms or condition will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of disorder; and supportive treatment, that is, treatment employed to supplement another specific therapy directed toward the improvement of the disorder. The term "treatment" also includes symptomatic treatment, that is, treatment directed toward constitutional symptoms of the disorder. "Treating" a condition with the compounds of the invention involves administering such a compound, alone or in combination and by any appropriate means, to an animal, cell, lysate or extract derived from a cell, or a molecule derived from a cell.

By "under conditions that allow interaction between a nucleic acid molecule and an RNA binding protein" is meant reaction conditions that permit a physical association between a nucleic acid molecule and a protein that is based on the specific characteristics of the interacting molecules, and is not inhibited by non-specific competitor molecules present at a concentration equivalent to the interacting molecules.

By a "UTR" is meant a nucleic acid sequence derived from the 5' or 3' untranslated region of a gene, wherein the sequence is composed of ten or more contiguous nucleotides, said nucleotides being outside of the coding region of a gene of interest. Preferably the UTR is the full length UTR sequence of a gene of interest, for example, the HER2 gene.

BRIEF DESCRIPTION OF THE DRAWINGS

FIG. 1C) or MCF7 cells stably transfected with a HER2-luciferase-HER2 chimeric construct (cell line 6D-2; FIG. 1D). Northern blots of RNA from fractions from sucrose density gradients of whole cell extracts were probed with either HER2 3' UTR cDNA (FIGS. 1A and 1B) or luciferase cDNA coding sequence (FIGS. 1C and 1D). Band intensities were quantitated by the Cyclone Storage Phosphor Screen (Packard) and plotted as a percent of total intensity from a given RNA species/gradient fraction.

FIG. 4 is the HER2 5' UTR sequence used to create the HER2-luciferase-HER2 construct described herein (SEQ ID NO: 1).

FIG. 5 is the HER2 3' UTR sequence used to create the HER2-luciferase-HER2 construct described herein (SEQ ID NO: 2).

DETAILED DESCRIPTION OF THE INVENTION

Figure 1:
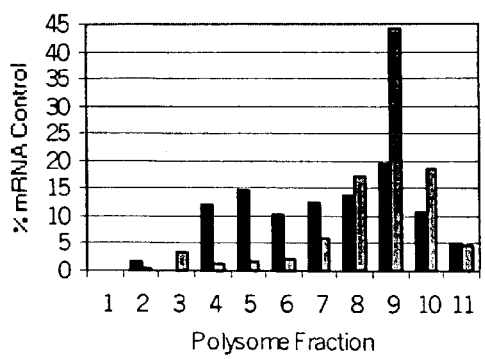
FIGS. 1A–1D are graphs of the results of polysome analysis of actin mRNA (lighter bars in FIGS. 1A–1D) and either HER2 RNA (darker bars in 1A and 1B), luciferase RNA (darker bars in 1C), or HER2-luciferase-HER2 chimeric RNA (darker bars in 1D). The cells used were HMEC (FIG. 1A), MCF7 cells (FIG. 1B), and MCF7 cells stably transfected with a luciferase construct (cell line 6D-1.
Figure 1:
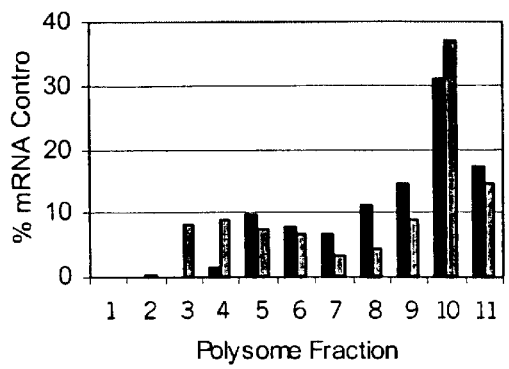
Figure 1:
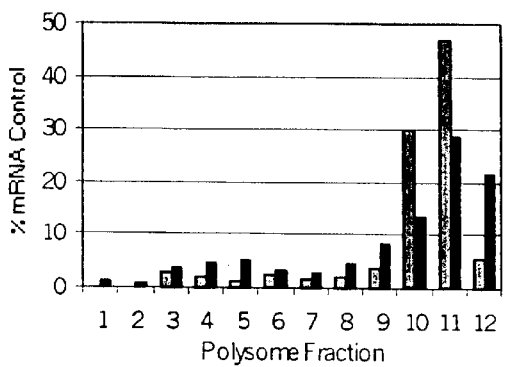
Figure 1:
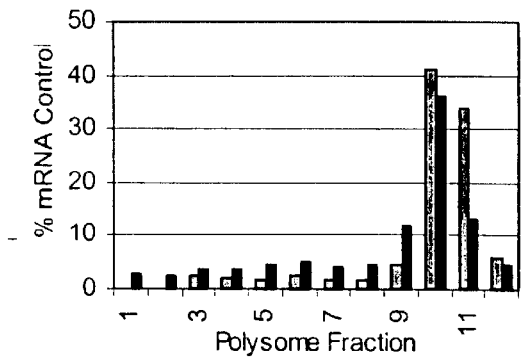

Assays for identifying compounds for use in treating or preventing a proliferative disease, e.g., by modulating the level of HER2 translation efficiency or by being toxic to selected cells, are described herein. These assays involve providing a cell comprising a HER2 regulatory element operatively linked to a reporter coding sequence and stably integrated into a chromosome of the cell; contacting the cell with a candidate compound; and assaying for an increase in cell death relative a cell not exposed to the candidate compound or assaying for a change in the level of translation efficiency of the reporter coding sequence in the cell, relative to a cell not exposed to the candidate compound. A modulation in the level of translation efficiency of the reporter coding sequence indicates a compound that modulates the translation efficiency of HER2.

The identified compounds can potentially be used in the treatment of proliferative diseases, such as various cancers. Several compounds have been identified by the assays of the present invention. These compounds were shown to be toxic to 6D-2 cells (MCF7 cells stably transfected with a HER2 5' UTR-luciferase-HER2 3' UTR chimeric construct), as described in detail below.

HER2 RNA Translation Efficiency

The overall expression level of a gene is controlled by a number of factors. RNA translation efficiency is one means by which gene expression is mediated. As discussed above, in eukaryotes, translational regulation usually occurs at the initiation step. Cis-elements in the 5' UTR, as well as the 3' UTR are important for regulating translation initiation. The cis-elements can be used in assays to identify compounds that affect the level of translation efficiency of a desired RNA in a cell.

HER2 has a 5'UTR of 178 nucleotides (nt), and there are two elements within this UTR that putatively could be strong regulators of translation. The first sequence is a stretch of GC-rich sequence between nucleotides 65 and 150 of the HER2 5' UTR. The second sequence is a short upstream open reading frame (uORF), from nucleotides 153 to 173 of the 5' UTR sequence, encoding a six-amino-acid peptide. The initiation codons for both the uORF and the authentic ORF are in good context for translation initiation (Seth et al., Br. J. Cancer 80: 657–669 (1999)). Geballe et al. found that HER2/neu is translated very efficiently in breast cancer cells even though it has an upstream open reading frame very close to the actual start site. In normal cells, however, translation of HER2/neu is inefficient.

The level of translation efficiency of HER2 can be detected as follows. A nucleic acid sequence containing a desired HER2 regulatory element, for example, the 5' or 3' UTR, be it a full-length UTR or a portion of a UTR, is operatively linked to a reporter nucleic acid sequence. The UTR sequence may comprise, for example, the full length sequence or a fragment of the HER2 5' or 3' UTR (SEQ ID NOS: 1 and 2, respectively; shown in FIGS. 4 and 5, respectively), which can be obtained from GenBank Accession Numbers M16789 (HER2 5 UTR) and X03363 (HER2 3' UTR). The reporter nucleic acid sequence may include, but is not limited to, nucleic acids encoding luciferase, β-galactosidase, chloramphenicol acetyltransferase, green fluorescent protein, and any RNA sequence that is not normally found in the cell in which the level of HER 2 RNA translation efficiency is being measured, but for which expression can be measured. The sequence may also include any other desired regulatory elements. In addition, a tag, for example a drug resistance marker, may also be incorporated into the nucleic acid sequence. This tag can then be used for identification of cells in which the HER2 UTR/reporter nucleic acid sequence is stably integrated.

The above-described HER2 UTR/reporter nucleic acid sequence, generally contained in a vector, is stably transfected into a cell of interest. Cells that may be used to measure translation efficiency include, but are not limited to mammary cells, for example, MCF7 mammary carcinoma cells, 6D-2 cells (MCF7 cells stably transfected with the HER2 UTR/luciferase construct described herein), ovarian cells, gastric cells, bladder cells, lung cells, or salivary gland cells. In another embodiment the cell is a cancer cell, for example, a mammary carcinoma cell, an ovarian cancer cell, a gastric cancer cell, a bladder cancer cell, a lung cancer cell, or a salivary gland carcinoma cell. Stable transfectants are then selected, for example, by drug selection if a selectable marker is incorporated into the vector. Alternatively, any method known to one skilled in the art may be used to identify and select for stably transfected cells.

To assess changes in HER2 translation efficiency, polysome distribution analysis may be performed on RNA isolated from the stably transfected cells, for example, as described by Johannes and Sarnow (RNA 4:1500–1513 (1998)). The polysome distribution analysis may be performed, for example, by centrifuging the isolated RNA through a sucrose gradient, separating the RNA isolated from the sucrose gradient fractions on formaldehyde-agarose gels, transferring the RNA to nitrocellulose, and probing the nitrocellulose with radiolabeled probes (e.g., cDNAs encoding the reporter gene). The amount of reporter RNA associated with high molecular weight (HMW) polysomes (i.e., contained in the same sucrose gradient fraction) is directly proportional to the level of HER2 translation efficiency, with high amounts of RNA associated with the HMW polysomes indicating high translation efficiency of HER2. If a UTR sequence mediates lower levels of HER2 translation efficiency, this effect will be seen by distribution of the reporter RNA sequence throughout the sucrose gradient, or the reporter sequence will be associated with only low molecular weight (LMW) polysomes, which are contained in a different fraction than the HMW polysomes.

Translation efficiency of HER2 can also be measured by determining the level of reporter protein expression or activity. For example, reporter protein levels can be assessed using any number of standard assays, including, but not limited to Western blotting techniques, ELISA, immunohistochemical techniques, and immunoprecipitation techniques. In addition, reporter protein activity can also be assessed using methods known to one skilled in the art, and the technique used to assay reporter protein activity will vary depending on the reporter protein used. For example, measuring reporter protein activity may involve measuring fluorescence (e.g., green fluorescent protein), enzymatic activity (e.g., β-galactosidase, luciferase, chloramphenicol acetyltransferase), toxicity (e.g., ricin), or an ability to be specifically bound by a second molecule (e.g., biotin or a detectably labeled antibody).

If the level of HER2 translation efficiency is measured by determining the level of reporter protein expression or activity, steady state RNA levels of the reporter nucleic acid sequences may also be determined. If steady state reporter RNA levels in a cell are not altered by a candidate compound exposed to the cell, yet the reporter protein expression or activity is altered as a result of administration of a candidate compound, then the candidate compound is a modulator of HER2 translation efficiency. Steady state level of an RNA of interest in a cell can be detected, for example, by treatment of the cells with actinomycin D followed by detection of the level of the-RNA of interest.

Screening for Compounds that Modulate HER2 Translation Efficiency

Identification of compounds that modulate HER2 translation efficiency can be accomplished by administering one or more candidate compounds to the cells to be tested for translation efficiency. Candidate compounds that modulate or affect the level of translation efficiency can be identified by comparing the level of translation efficiency of HER2 RNA isolated from a cell exposed to the candidate compound with the level of translation efficiency of HER2 RNA isolated from a cell not exposed to the candidate compound, or exposed to vehicle only. Candidate compounds that modulate the level of translation efficiency will be identified if the levels of translation efficiency in the two samples differ. A compound can directly modulate HER2 translation efficiency, for example, by binding to the HER2 RNA. Alternatively, a candidate compound can indirectly modulate translation efficiency of HER2 RNA by interacting with one or more proteins that bind to the RNA and alter an RNA binding protein's ability to participate in the translation of the RNA. In addition, a candidate compound can alter the expression of a protein or polypeptide involved in translation of the HER2 RNA, thereby modulating HER2 RNA translation efficiency.

Assays measuring HER2 translation efficiency of a control cell can be performed separately from, or together with, the assays of the test cells. When performed separately, the control cell assay can be performed either before, after, or simultaneous with the test cell assays. It is desirable that the control cell assay be performed simultaneously with the test cell assays. In addition, the HER2 UTR/nucleic acid sequence may further contain any other regulatory element of interest.

If desired, RNA binding proteins can be added to the assay to determine the effect of a combination of a candidate compound and an RNA binding protein on HER2 translation efficiency. RNA binding proteins can be identified and isolated according to the methods described in U.S. Ser. No. 09/165,868, filed Oct. 2, 1998, incorporated herein by reference. The RNA binding protein may be administered to the cell under conditions that allow interaction between the HER2 UTR and the RNA binding protein, and such conditions are known in the art. Identification of a candidate compound that modulates HER2 translation efficiency differently when in the presence of an added RNA binding protein may provide information regarding the mechanism of action of the candidate compound. In addition, the interaction between the RNA binding protein and the HER2 UTR may occur through direct interaction, or it may be mediated by one or more polypeptides. The identification of the polypeptides involved in a binding interaction can be identified using standard molecular biology techniques, and as described in U.S. Ser. No. 09/165,868.

Compounds identified as modulators of HER2 RNA translation efficiency can be used to affect the function or expression of HER2 in a cell in vivo or ex vivo. The identification of such compounds can also lead to the development of therapies to treat or prevent a number of disease or conditions, for example, cancer and other proliferative diseases.

Toxicity and Growth Inhibition Assays

The viability of a cell contacted with a candidate compound may also be used to screen for compounds that are useful for treating or preventing proliferative diseases. Reduced HER2 protein expression in tumor cells has been shown to be associated with cell toxicity (Juhl et al., J. Biol. Chem. 272:29482–29486 (1997)). Therefore, a compound that decreases the translation efficiency of HER2 will result in increased cell death, compared to control cells that are not administered the compound, or that are contacted with the compound vehicle only. In addition, an assay based on viability of cells will detect compounds whose toxicity is mediated by another mechanism. Methods for assaying cell death are well known in the art. For example, cell death can be measured by determining cellular ATP levels, wherein a cell that is undergoing cell death has a decreased level of cellular ATP compared to a control cell. Cell death may also be measured by staining with a vital dye, for example, trypan blue, wherein a cell that is dying will be stained with the vital dye, and a cell that is not dying will not be stained with the dye.

In some instances, inhibition of cell growth may be sufficient for a therapeutic effect. As such, assays for cell viability may also be used to determine if candidate compounds inhibit cell growth. Inhibition can be measured, for example by determining by standard means the number of cells in a population contacted with the candidate compound compared to the number of cells in a population not contacted with the candidate compound. If the number of cells in the population contacted with the candidate compound does not increase over time or increases at a reduced rate compared to cells not contacted with the compound, the candidate compound inhibits the growth of the cells. A similar assay may also be performed to determine if a compound stimulates growth.

In the present invention, cells containing a nucleic acid sequence including a HER2 regulatory element operatively linked to a reporter coding sequence may also be used to determine cell viability. As cells die or stop growing, the population of these cells produces a lower amount of the reporter sequence, and this reduction can be used to quantify the toxicity or growth inhibition of candidate compounds. Alternatively, cell viability can be assayed by any method known in the art. In one embodiment, the effect of a candidate compound to a cell characteristic of a proliferative disease is compared to the effect of the compound to a cell representative of the general cell population of an organism. A compound that is more toxic or growth inhibitory to a proliferative disease cell than a general cell is a potential therapeutic agent for the proliferative disease.

High Throughout Screening Assay

Although not required, compounds can be detected in an automated manner using, for example, automated detection of HER2 translation efficiency and comparison of such efficiencies between cells treated with candidate compounds (potential modulators of HER2 translation efficiency) and controls that are not administered the compound, or that are administered the compound vehicle only. As described herein, the screening assay utilizes reporter nucleic acid sequences, for example, luciferase, operatively linked to HER2 UTR regulatory element(s). Such reporter sequences are designed for rapid detection, and provide a means for high throughput screening of compounds. Reagents and methods for the use and detection of the reporter nucleic acid sequences described herein are well known. The rate of screening is also increased by carrying out the screen in a multi-well format, using, for example, 96- or 384-well plates in which the reporter activity can be assayed in a plate reader. High-throughput screening may also be employed in assays measuring toxicity or growth inhibition using similar techniques.

Additional Potential Therapeutic Compounds

Once a candidate compound is identified as a possible therapeutic for a proliferative disease, e.g., cancer, that compound may be used as the basis for a structure-activity relationship (SAR) study to identify other structurally related potential therapeutics. A SAR study may be performed using methods well known in the art. The synthesis of these structurally related compounds is known to one skilled in the art. A general synthetic scheme is shown in Scheme 1.

Compounds identified by the screens of the inventions or through a SAR, may be derivatized, e.g., to enhance bioavailability, solubility, or stability in vivo or ex vivo, or to reduce the toxicity to non-target cells or dosage required. In addition, the compounds of the invention may be in the form of pharmaceutically acceptable salts.

Preliminary data indicate that compounds having pyrrolidine substituents at position 3 of the napthoquinone compounds (position 6 of the isoquinoline and quinoline compounds) have higher activity than compounds with four- or six-membered substituents. Lower activity, however, may be desirable in certain instances. In addition, substituted four-membered rings may mimic a five-membered ring and thus show increased activity.

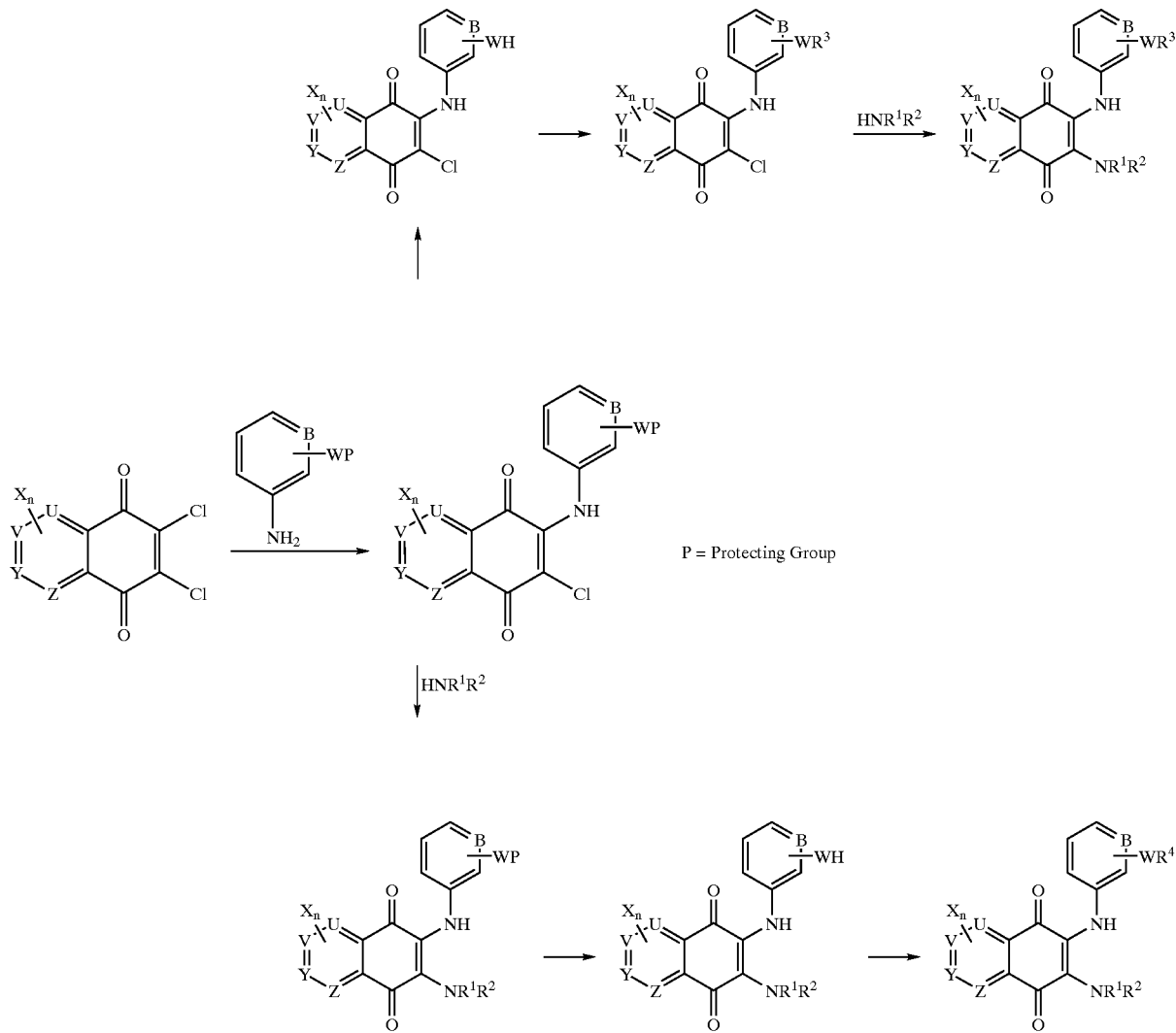

Therapy

A compound identified by any of the above-described methods may be administered within a pharmaceutically acceptable diluent, carrier, or excipient, in unit dosage form. Conventional pharmaceutical practice may be employed to provide suitable formulations or compositions to administer the identified compound to patients suffering from a proliferative disease. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (19th ed., A. R. Gennaro, ed., 1995, Mack Publishing Company, Easton, Pa.). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyetbylene-polyoxypropylene copolymers may be used to control the release of the compounds. Other potentially useful parenteral delivery systems for compounds that modulate HER2 translation efficiency include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound identified according to the methods described above, may be combined with more traditional therapies for a proliferative disease, for example, traditional chemotherapeutic agents, radiation therapy, or surgery. In addition, these methods may be used to treat any subject, including mammals, for example, humans, domestic pets, or livestock.

The criteria for assessing response to therapeutic modalities employing an identified compound is dictated by the specific condition and will generally follow standard medical practices. Generally, the effectiveness of administration of the compound can be assessed by measuring changes in characteristics of the disease condition.

Identifying Regions in HER2 UTRs that Alter the Level of HER2 RNA Translation Efficiency Regions in HER2 RNA molecules that alter the level of HER2 RNA translation efficiency are identified by making reporter constructs, as described herein, consisting of successively smaller fragments of a larger HER2 UTR nucleic acid molecule operatively linked to a reporter nucleic acid sequence. Alternatively, reporter constructs are made in which a HER2 UTR nucleic acid molecule contains one or more mutations or deletions. These reporter constructs may also contain any other desired regulatory elements. The reporter constructs are transformed into a cell, to generate stably transfected cells. The effect of the RNA molecules on the level of HER2 translation efficiency is then measured, either alone or in the presence of a candidate compound if so desired, using methods described herein. By comparing the translation efficiency of the truncated or mutated HER2 nucleic acid molecules to the levels of translation efficiency mediated by full length or unmutated HER2 nucleic acid molecules, the region(s) of HER2 nucleic acid molecules involved in mediating translation efficiency can be identified.

The following examples are to illustrate the invention. They are not meant to limit the invention in any way.

EXAMPLE 1

Translation Efficiency Analysis of HER2 Gene Expression

HER2 is an example of a gene whose post-transcriptional control is altered in breast cancer. It has been determined that the level of RNA translation efficiency of HER2 RNA is altered in breast cancer cell lines compared to primary cells. Specifically, the translational repression of HER2 is de-regulated in cancer cells. This was determined by measuring the efficiency of translation by polysomal distribution analysis, an assay in which efficiently translated RNA, which is associated in the cell with high molecular-weight (HMW) polysomes, migrates further in sucrose density gradients than non-translated or poorly translated RNA, which migrates more slowly in sucrose density gradients.

To confirm that the level of HER2 translation efficiency is altered in breast cancer cell lines compared to primary cells, endogenous HER2 RNA was subjected to polysomal distribution analysis, using primary cells from human mammary epithelial cells (HMECs) and the transformed breast cancer cell line MCF7. The polysomal distribution analysis was performed as described by Johannes and Sarnow (supra). The translation efficiency of actin RNA was monitored as a control in the polysomal distribution analysis. In HMECs, actin RNA was located predominantly on HMW polysomes, since actin mRNA is translated with high efficiency in these cells (FIG. 1A; lighter bars). In contrast, HER2 RNA from HMECs was much more evenly distributed throughout the gradient, indicating much less efficient translation (FIG. 1A; darker bars). Therefore, HER2 RNA was translationally repressed in HMEC cells, as would be expected from the structure of its 5' UTR, which includes a short upstream open reading frame (uORF), which is known to repress translation of major open reading frames.

When polysome distribution analysis of MCF7 cells was performed, again actin RNA was found primarily in the HMW polysome fraction, confirming efficient translation of this RNA in MCF7 cells (FIG. 1B; lighter bars). HER2 RNA in MCF7 cells was also efficiently translated, as indicated by the significant fraction of HER2 RNA in the HMW polysome fraction (FIG. 1B; darker bars). This finding is in contrast to the result found in HMECs and has been confirmed by others.

To examine the effect of HER2 UTRs specifically on the level of HER2 RNA translational efficiency, the full-length 5' and 3' HER2 UTRs (SEQ ID NOS: 1 and 2, respectively) were operatively linked to a luciferase reporter coding nucleic acid sequence, using standard recombinant DNA technologies. The HER2 5' and 3' UTR sequences are provided in FIGS. 4 and 5, respectively. The HER2 UTR/reporter nucleic acid sequence was subcloned into the pRc/RSV expression plasmid, and stably transfected into MCF7 cells, using standard molecular biology techniques, for example, as described by Ausubel et al. (*Current Protocols in Molecular Biology*, John Wiley & Sons, New York, N.Y., 1998). As a control, a construct containing the luciferase coding sequence without any HER2 5' or 3' UTR sequence was also made and stably transfected into MCF7 cells. Cells stably transfected with the constructs were selected in G418 media (500 μg/ml).

To assess changes in the level of HER2 RNA translation efficiency due to the HER2 5' and 3' UTRs, polysome analysis was performed on stably transfected RNA from the two cell populations grown to near confluency, as described above. Briefly, RNA isolated from the sucrose gradients was separated on formaldehyde-agarose gels, transferred to nitrocellulose, and probed with radiolabeled cDNAs encoding luciferase using hybridization conditions of 65 C, 40 mM sodium phosphate, 1 mM EDTA, and 1% sodium dodecyl sulfate overnight. In the sample obtained from stable transfectants containing the luciferase nucleic acid sequence only, the luciferase reporter RNA was found associated with HMW polysomes (FIG. 1C). In addition, RNA isolated from the stable transfectants containing luciferase operably linked to the 5' and 3' UTR of HER2 was also associated primarily with HMW polysomes (FIG. 1D). These data indicate that neither the 5' UTR, despite the presence of the GC-rich element and the uORF just upstream of the initiation codon, nor the 3' UTR were barriers to high levels of translation efficiency. Thus, the stable chimeric constructs behaved as endogenous HER2 RNA in MCF7 cells (compare FIGS. 1B and 1D), and a screening system has been established to identify compounds that modulate the translation efficiency of HER2.

Figure 2:
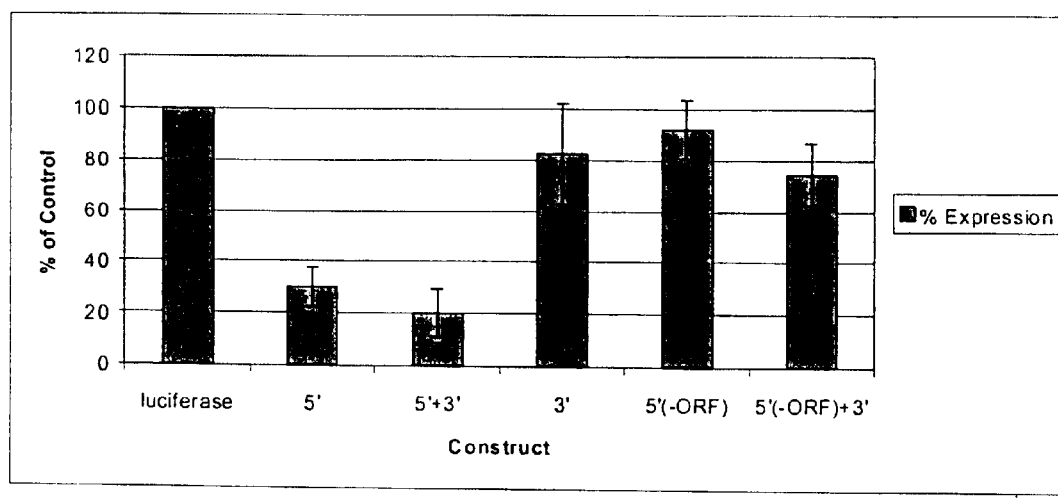
FIG. 2 is a graph showing luciferase reporter enzyme activity from transiently transfected constructs in MCF7 cells. Activities were controlled for transfection efficiency by co-transfecting with a Renilla luciferase gene-containing plasmid. Activities were recorded as a percent of the luciferase-alone activity (first bar). The HER2-luciferase-HER2 chimeric reporter constructs tested are shown below each activity bar. HER2-luciferase-HER2 chimeric reporter constructs with deletions of the uORF are denoted as (-ORF).

To address the possibility that the MCF7 cells are incapable of modulating the level of translation efficiency through the HER2 5' or 3' UTR sequences, we transiently transfected expression constructs containing the HER2 UTRs with or without the uORF into MCF7 cells, and measured luciferase RNA levels and reporter enzyme activity. Cells transfected with luciferase constructs containing the full-length HER2 5' UTR (with or without the 3' UTR) resulted in nearly five-fold less reporter activity than those cells transfected with constructs containing the luciferase reporter alone (FIG. 2). Furthermore, when the luciferase reporter construct contained the HER2 5' UTR but with a deletion of the 21-nt uORF sequence, activity was nearly completely restored.

In the above-described transient transfection studies, steady state RNA levels in the transiently transfected MCF7 cells did not correlate with luciferase enzyme activity, indicating that the differences in luciferase reporter activity in this system were not due to differences in steady state RNA levels, assayed using standard conditions, but rather due to changes in translational efficiency of the chimeric HER2/luciferase RNAs.

The above results of the transient transfection assays revealed that the MCF7 cells do indeed have the capacity to negatively regulate translation via the uORF element in the HER2 5' UTR, but that they do not have this capacity when the HER2 RNA is endogenous or when luciferase RNA operatively linked to the HER2 UTRs is stably transfected into the cells. The use of a screening system in which the HER2 UTR/nucleic acid molecule is stably integrated in the genome of the cell more accurately reflects the molecular organization of HER2 in cells that overexpress HER2, for example, cancer cells. Therefore, a screening system that utilizes a stably integrated HER2 UTR/reporter nucleic acid sequence is preferable.

To examine how the decay rate of the HER2 UTR/reporter nucleic acid sequence compared to the decay rate of endogenous HER2 RNA, RNA decay rates in the stably transfected cell lines were measured. RNA decay rates were measured after treatment of the cells with actinomycin D (5 μg/ml) for up to 8 hours, using standard methods. In MCF7 cells stably transfected with the luciferase construct without any HER2 UTRs, the half-life of the luciferase RNA was approximately 4 hours. In contrast, MCF7 cells stably transfected with the luciferase construct containing both 5' and 3' HER2 UTRs displayed a half-life of only approximately 1 hour. In both cell lines, the decay rate of endogenous HER2 RNA showed an initial decrease of 40% after 0.5 hours, followed by a leveling off throughout the rest of the time course. This initial decrease in endogenous HER2 RNA levels mimicked in slope and magnitude the initial decrease in RNA observed for the stably transfected chimeric HER2 UTR/reporter nucleic acid sequences. The apparent biphasic profile was also observed when the decay rate of endogenous HER2 from untransfected cells was assayed. These data suggest that the UTRs can confer the initial instability on a reporter, as well as the endogenous gene, while the stability aspect of the curve must be attributed to elements in the coding sequence. These data also again demonstrate that our HER2 UTR/reporter nucleic acid system stably transfected into MCF7 cells is an optimal system for identifying compounds that modulate HER2 translation efficiency.

EXAMPLE 2

Screening Assay to Identify Compounds for the Treatment or Prevention of a Proliferative Disease The HER2 UTR/reporter nucleic acid stably transfected cell system described above was used to identify compounds that either increased or decreased the level of HER2 translation efficiency. Small molecules from a library of candidate compounds (MES library, Message Pharmaceuticals, Malvern, Pa., containing, for example, small molecules from a commercially available Nanoscale Combinatorial Synthesis Inc. (Mountain View, Calif.) library) were administered to 6D-2 cells containing the stably transfected luciferase reporter nucleic acid sequence operatively linked to HER2 5' and 3' UTRs to identify compounds that modulate HER2 translation efficiency. Each candidate compound was administered at a concentration of 10 μM.

After 16 hours of exposure to the compound, the level of luciferase protein activity was measured in candidate compound-treated cells containing the luciferase construct only, or in cells containing the luciferase/UTRs that were not treated with the candidate compound, or are treated with the candidate compound vehicle only (control cells), and compared to activity levels in candidate compound-treated cells containing the luciferase construct with the UTRs (test cells). The level of HER 2 RNA translation efficiency was increased by a candidate compound when the level of luciferase protein expression or activity was increased in the test cells, compared to the control cells. Conversely, HEP2 RNA translation efficiency was decreased by a candidate compound when the level of luciferase protein expression or activity was decreased in the test cell, compared to the control cell.

MES 51151

As described above, candidate compounds from a small molecule library (MES library, Message Pharmaceuticals, Malvern, Pa., containing, for example, small molecules from a commercially available Nanoscale Combinatorial Synthesis Inc. (Mountain View, Calif.) library) were tested in order to identify compounds that modulate HER2 translation efficiency. Using the above described HER2 5' and 3' UTR/ reporter nucleic acid stably transfected MCF7 system, one such compound has been identified. This compound, MES 51151 (from the Nanoscale Combinatorial Synthesis Inc. library; Compound Identification Number: NS13278), has the structure:

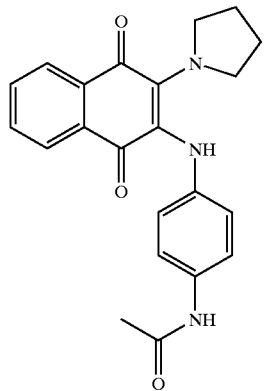

Figure 3:
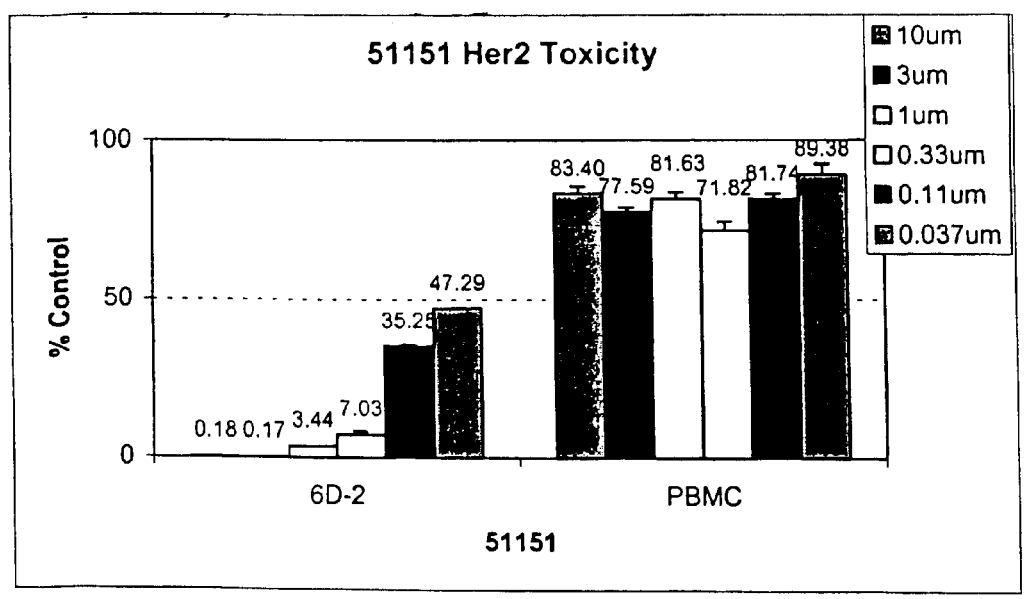
FIG. 3 is a graph of the effect of administration of MES51151 on the viability of 6D-2 cells and PBMCs.

It was determined that MES 51151 reduced luciferase activity through toxicity. Toxicity of the transfected cells increased with increased concentration of MES 51151 administered to the cells (FIG. 3, showing the percent viable 6D-2 cells compared to control cells). MES 51151 was administered to primary peripheral blood mononuclear cells (PBMCs) to test for its effect on cell toxicity. MES51151 was not toxic to the PBMCs (FIG. 3, showing the percent viable PBMCs compared to control cells). The EC50 of MES 51151 when administered to the 6D-2 cancer cell line was less than 100 nM, yet MES 51151 was not toxic to PBMCs even when administered at a concentration of 10 $\mu$M. Therefore, the therapeutic index of MES 51151 is at least 100, and may be even higher. The results of these assays demonstrate that MES 51151 is preferentially toxic to cancer cells compared to PBMCs. Thus, this compound may potentially be employed for the treatment or prevention of proliferative diseases, including cancer.

Examples 3–30 detail the synthesis of compounds potentially useful for the treatment or prevention of proliferative diseases. These compounds were identified by a structure activity relationship based on MES 51151.

EXAMPLE 3

6-(N'-4-aminoacetanilide)-7-pyrrolidino-5,8-isoquinolinedione (MES 10555) and 7-(N'-4-aminoacetanilide)-6-pyrrolidino-5,8-isoquinolinedione (MES 10556)

2,3-dichloro-1,4-isoquinoline (0.5 mmol, 114 mg) was dissolved in anhydrous DMF (1.5 mL) in a 5 mL vial. 4-aminoacetanilide (0.5 mmol, 75 mg) and triethylamine (0.5 mmol, 70 $\mu$L) were added. The solution was heated at 100° C. for 6 hr. Pyrrolidine (2 mmol, .0.33 mL) was added. The solution was heated at 100° C. for 16 hr. Flash chromatography on silica gel eluted with EtOAc/Hexane (85:15) gave a green solid (60 mg). This green solid was dissolved in acetonitrile and further purified with HPLC to give two components:

A. 6-(N'-4-aminoacetanilide)-7-pyrrolidino-5,8-isoquinolindeione (MES 10555) (21 mg) as a dark green solid. $^1$H NMR (CDCl$_3$): $\delta$=9.22 (s, 1H), 8.94 (d, 2H, J=4.79 Hz), 7.79 (d, 1H, J=4.79 Hz), 7.37 (d, 2H, J=8.75 Hz), 7.06 (s 1H), 6.94 (s, 1H), 6.21 (d, 2H, J=8.75 HZ), 3.51–1.43 (m, 4H), 2.17 (s, 3H), 1.69–1.62 (m, 4H) ppm.

B. 7-(N'-4-aminoacetanilide)-6-pyrrolidino-5,8-isoquinolinedione (MES 10556) (7.5 mg) (dark green solid). $^1$H NMR (CDCl$_3$): $\delta$=9.21 (s, 1H), 8.95 (d, 1H, J=4.80 Hz), 7.80 (d, 1H, J=4.80 Hz), 7.43 (d, 2H, J=8.75 Hz), 6.82 (d, 2H, J=8.75 Hz), 6.76 (s, 1H), 3.61–3.52 (m, 4H), 2.19 (s, 3H), 1.69–1.61 (m, 4H) ppm.

EXAMPLE 4

6-(N'-4-fluoroanilino)-7-pyrrolidino-5,8-isoquinolinedione (MES 10557)

The title compound was prepared in a manner analogous to Example 3, by substituting 4-fluoroaniline (0.5 mmol, 55.5 mg) for 4-aminoacetanilide. $^1$H NMR (CD$_3$OD): $\delta$=9.06 (s, 1H), 8.80 (d, 1H, J=8.4 Hz), 7.84 (d, 1H, J=8.4), 6.88 (dd, 2H, J=10.8, 10.2 Hz), 6.59 (dd, 2H, J=10.2, 6.0), 3.43–1.36 (m, 4H), 1.56–1.50 (m, 4H) ppm.

EXAMPLE 5

6-(N-4-fluoroanilino)-7-pyrrolidino-5,8-quinolinedione (MES 10563).

6,7-dichloro-5,8-quinolinedione (0.5 mmol, 114 mg) was dissolved in anhydrous DMF (1.5 mL) in a 5 mL vial. 4-fluoroaniline (0.5 mmol, 75 mg) and triethylamine (0.5 mmol, 70 $\mu$L) were added. The solution was heated at 100° C. for 16 hr. Pyrrolidine (2 mmol, 0.17 mL) was added. The solution was heated at 100° C. for 24 hr. The excess amines were removed under vacuum. The resulting blue oil was dissolved in acetonitrile (1% TFA) and purified by HPLC to give the title compound (38.5 mg) as a dark green solid. $^1$H NMR (CDCl$_3$): $\delta$=8.95 (dd, 1H, J=6.6, 1.2 Hz), 8.42 (dd, 1HH, J=8.4, 1.2 Hz), 7.67 (dd, 1H, J=8.4, 6.6 Hz), 6.65 d, 2H, J=10.8, 10.2 Hz), 6.61 (dd, 2H, J=10.2, 6.0), 3.58–3.51 (m, 4H), 1.73–1.67 (m, 4H) ppm.

EXAMPLE 6

N-4-((3-pyrrolidino-1,4-naphthalenedion-2-yl) amino)phenyl-O-1,1-dimethylethylcarbamate (MES 10553)

2,3-dichloro-1,4-naphthoquinone (1 mmol, 227 mg) was dissolved in anhydrous DMF (3.0 mL) in a 20 mL vial. N-tBOC-phenylenediamine (1.0 mmol, 208 mg) and triethylamine (1.0 mmol, 140 $\mu$L) were added. The solution was heated at 100° C. for 2 hr. Pyrrolidine (4 mmol, 0.33 mL) was added. The solution was heated at 100° C. for 16 hr. The solution was poured in water (10 mL). The mixture was extracted with methylene chloride (2×20 mL). The combined organic layers were washed with 0.1N HCl (2×10 mL) and dried (Na$_2$SO$_4$). The solution was concentrated in vacuum to give a green solid (0.45 g). Flash chromatography on silica gel eluted with EtOAc/Hexane (1:1) gave a dark green solid (300 mg). $^1$H NMR (CDCl$_3$): 8.03–7.96 (m, 2H), 7.62–7.54 (m, 2H), 7.19 (d, 2H, J=8.48 Hz), 6.82 (s, 1H), 6.58 (d, 1H, J=8.48 Hz), 3.60–7.53 (m, 4H), 2.23 (s, 3H), 1.66–1.58 (m, 4H), 1.50 (s, 9H) ppm.

EXAMPLE 7

2-(N-4-aminoanilino)-3-pyrrolidino-1,4-naphthoquinone (MES 10554)

Example 6 (150 mg) was dissolved in 4 mL 50% TFA/CH$_2$Cl$_2$. The purple solution was stirred at rt for 1 h. The solvent was removed under vacuum to give 124 mg of the title compound. $^1$H NMR (DMSO-d$_6$): 7.23–7.16 (m, 2H), 6.93–6.85 (m, 2H), 6.38 (d, 2H, J=8.68 Hz), 5.94 (d, 2H, J=8.68 Hz), 4.03 (s, 2H), 2.76–2.69 (m, 4H), 1.97 (s, 1H), 0.92–0.86 (m, 4H) ppm.

EXAMPLE 8

2-(N-2-methoxy-5-aminopyridine)-3-pyrrolidino-1,4-naphthoquinone (MES 10559)

2,3-dichloro-1,4-naphthoquinone (0.5 mmol, 114 mg) was dissolved in anhydrous DMF (1.5 mL) in a 5 mL vial. 5-Amino-2-methoxypyridine (0.5 mmol, 62 mg) and triethylamine (0.5 mmol, 70 μL) were added. The solution was heated at 70° C. for 16 hr. Pyrrolidine (2 mmol, 0.17 mL) was added. The solution was heated at 70° C. for 16 hr. Flash chromatography of crude product (1.0 mL) on silica gel eluted with EtOAc/Hexane (1:9) gave a dark green solid (73.1 mg). $^1$H NMR (CDCl$_3$): 8.05–7.95 (m, 2H), 7.68–7.59 (m, 2H), 7.02 (d, 1H, J=6.0 Hz), 6.79 (s, 1H), 6.62 (d, 1H, J=6.0 Hz), 3.9 (s, 3H), 3.52–1.43 (m, 4H), 1.65–1.56 (m, 4H) ppm.

EXAMPLE 9

2-(N-4-methoxyanilino)-3-pyrrolidino-1,4-naphthoquinone (MES 10564)

2,3-dichloro-1,4-naphthoquinone (1.0 mmol, 227 mg) was dissolved in anhydrous DMF (3.0 mL) in a 20 mL vial. 4-Methoxyaniline (1.0 mmol, 123 mg) and DIEA (1.0 mmol, 173 μL) were added. The solution was heated at 100° C. for 6 hr. Pyrrolidine (4 mmol, 0.33 mL) was added. The solution was heated at 100° C. for 16 hr. Flash chromatography of crude product (1.0 mL) on silica gel eluted with EtOAc/Hexane (1:9) gave a dark green solid (57 mg). $^1$H NMR (CDCl$_3$): 8.15–8.06 (m, 2H), 7.69–7.60 (m, 2H), 6.84 (d, 1H, J=8.5 Hz), 6.63 (d, 1H, J=8.5 Hz), 3.88 (s, 1H), 3.78 (s, 3H), 3.50–3.39 (m, 4H), 1.64–1.56 (m, 4H) ppm.

EXAMPLE 10

7-((3-pyrrolidino-1,4-naphthalenedion-2-yl)amino)-4-methylcoumarin (MES 10567)

2,3-dichloro-1,4-naphthoquinone (0.5 mmol, 114 mg) was dissolved in anhydrous DMF (1.5 mL) in a 5 mL vial. 7-Amino-4-methylcoumarin (0.5 mmol 88 mg) and triethylamine (0.5 mmol, 70 μL) were added. The solution was heated at 100°C. for 16 hr. Pyrrolidine (2 mmol, 0.17 mL) was added. The solution was heated at 100° C. for 16 hr. The excess volatile amines were removed under vacuum. The residue was dissolved in 3 mL acetonitrile containing 1% TFA. The crude product (1.0 mL) was purified with HPLC to give a dark purple solid (26.3 mg). $^1$H NMR (CDCl3): 8.09–7.98 (m, 2H), 7.64–7.55 (m, 2H), 7.45 (d, 1H, J=8.6 Hz), 6.74 (d, 1H, J=8.6 Hz), 6.31 (s, 1H), 6.09 (s, 1H), 3.63–3.54 (m, 4H), 2.36 (s, 3H), 1.78–1.69 (m, 4H) ppm.

EXAMPLE 11

N$^1$-4-((3-pyrrolidino-1,4-naphthalenedion-2-yl)amino)phenyl-N$^2$-(1-methylethyl)thiourea (MES 10571)

Example 7 (0.30 mmol, 100 mg) was dissolved in anhydrous DMF (3.5 mL). Triethylamine (0.2 mL) and isopropylisothiocyanate (0.45 mmol, 48 μL) were added. The solution was stirred at rt for 16 h. HPLC purification of the reaction solution (0.7 mL) gave 9.5 mg of MES 10571. 1H NMR (CDCl$_3$): 8.07–7.98 (m, 2H), 7.69–7.58 (m, 2H), 7.4 (bs, 1H), 7.04 (d, 2H, J=9.8 Hz), 6.65 (d, 2H, J=9.8 Hz), 4.66 (m, 1H), 3.60–3.50 (m, 4H), 1.72–1.62 (m, 4H)., 1.19 (d, 6H, J=6.0 Hz) ppm.

EXAMPLE 12

N$^1$-4-((3-pyrrolidino-1,4-naphthalenedion-2-yl)amino)phenyl-N$^2$-methylthiourea (MES 10572)

The title compound (15.2 mg) was produced similarly to Example 11 by treatment of Example 7 with methyl isothiocyanate. $^1$H NMR (CDCl$_3$): 8.06–7.95 (m, 2H), 7.66–7.58 (m, 2H), 7.52 (s, 1H), 7.07 (d, 2H, J=9.8 Hz), 6.65 (d, 2H, J=9.8 Hz), 5.8 (bs, 1H) 3.61–3.48 (m, 4H), 3.13 (s, 3H), 1.79–1.60 (m, 4H) ppm.

EXAMPLE 13

2-(N-3-aminoacetylanilino)-3-pyrrolidino-1,4-naphthoquinone (MES 10619)

To a solution of 2,3-dichloro-1,4-naphthoquinone (2 mmol) in dry DME (5 mL) was added 3-aminoacetanilide (2 mmol) and triethylamine (2 mmol). The reaction mixture was heated to 100° C. for 2 hr, or until no dichloroquinone was present by TLC, and then adsorbed onto dry silica gel. Chromatography on silica gel eluted with hexanes/ethylacetate (1:1–1:7) gave 2-(N-3-aminoacetylanilino)-3-dichloro-1,4-naphthoquinone as a red solid. 2-(N-3-aminoacetylanilino)-3-dichloro-1,4-naphthoquinone (0.05 mmol) was dissolved in DMSO (250 μL) and to this added pyrrolidine (42 μL), and the mixture heated to 50° C. for 24 hr, or until no intermediate 3-chloroquinone was present by TLC. The reaction mixture was partitioned between ethylacetate and water. The organic phase was separated and washed with water (3×) and brine, and dried over sodium sulfate. The resultant amorphous purple powder can be crystallized from hexanes/ethylacetate to give the title compound. $^1$H NMR (DMSO-d$_6$): δ=9.72 (s, 1H), 7.91 (m, 2H), 7.73 (m, 2H), 7.59 (s, 1H), 7.03 (t, 1H), 6.93 (br d, 1H), 6.82 (s, 1H), 6.48 (br d, 1H), 3.43 (m, 4H), 1.98 (s, 3H), 1.56 (m, 4H) ppm.

EXAMPLE 14

2-(N-anilino)-3-pyrrolidino-1,4-naphthoquinone (MES 10620)

To a solution of 2,3-dichloro-1,4-naphthoquinone (2 mmol) in dry DMF (5 mL) was added aniline (2 mmol) and triethylamine (2 mmol). The reaction mixture was heated to 50° C. for 2 hr, or until no dichloroquinone is present by TLC. The reaction mixture was partitioned between ethyl acetate (200 mL) and water (200 mL). The organic phase was washed with water (4×200 mL) and then brine (200 mL) and subsequently adsorbed onto dry silica gel. Chromatography on silica gel eluted with hexanes/ethylacetate (1:1–0:1) gave 2-anilino-3-dichloro-1,4-naphthoquinone as a red solid. 2-anilino-3-dichloro-1,4-naphthoquinone (0.2 mmol) was dissolved in DMSO (1 mL) and to this added pyrrolidine (168 μL), and the mixture heated to 50° C. for 24 hr, or until no intermediate 3-chloroquinone is present by TLC. The reaction mixture was partitioned between ethylacetate and water. The organic phase was separated and washed with water (3×) and brine, and dried over sodium sulfate. Evaporation of solvent gave a purple glassy solid. $^1$H NMR (DMSO-d$_6$): δ=7.91 (m, 2H), 7.74 (m, 2H), 7.59 (s, 1H), 7.14 (m, 2H), 6.73 (m, 1H), 6.66 (m, 2H), 3.45 (m, 4H), 1.55 (m, 4H) ppm.

EXAMPLE 15

2-(N-4-aminobenzoylanilino)-3-pyrrolidino-1,4-naphthoquinone (MES 10622)

A solution of 2,3-dichloro-1,4-naphthoquinone (5.0 g, 22 mmol, 1 eq) and p-phenylenediamine (4.75 g, 44 mmol, 2 eq) in DMF (100 ml) was stirred at room temperature for 2 hours and then mixed with water (1 L). Purple solids were collected by filtration and dried under reduced pressure to give 2-(N-4-aminoanilino)-3-chloro-1,4-naphthoquinone (6.4 g, 21.4 mmol, 97.5%).

A solution of 2-(N-4-aminoanilino)-3-chloro-1,4-naphthoquinone (500 mg, 1.68 mmol, 1 eq) and benzoyl chloride (234 L, 2.02 mmol, 1.2 eq) in DMF (10 ml) was stirred at room temperature for 2 hours. After this time, the solution was partitioned between ethyl acetate (100 ml) and water (100 ml). The organic phase was washed with water (4×100 ml). Removal of the ethyl acetate gave a red crude solid. The crude solid and pyrrolidine (1.4 ml, 16.9 mmol, 10 eq) in DMF (10 ml) was stirred at 50° C. for 4 hours. The reaction mixture was then partitioned between ethyl acetate (150 ml) and water (150 ml). The organic phase was washed with water (4×150 ml) and brine (150 ml) and dried over $Na_2SO_4$. Removal of the solvent gave a solid. The crude solid was passed through a silica gel. Evaporation of the solvent under reduced pressure gave a green solid, which was dried under vacuum (232 mg, 32% yield). A portion of the product was further purified using flash column chromatography ($SiO_2$, EtOAc/petroleum ether, 1:5, 3 consecutive columns) to obtain a sample of good purity. $^1H$ NMR (DMSO-$d_6$): δ=10.02 (s, 1H), 7.91 (m, 4H), 7.74 (m, 2H), 7.72 (s, 1H), 7.52 (m, 5H), 6.99 (d, 2H), 3.43 (m, 4H), 1.57 (m, 4H) ppm.

EXAMPLE 16

2-(N-3-fluoroanilino)-3-pyrrolidino-1,4-naphthoquinone (MES 10626)

To a solution of 2,3-dichloro-1,4-naphthoquinone (2.0 mmol) in dry DME (2.0 mL) was added 3-fluoroaniline (2.0 mmol) and ethyldi(isopropyl)amine (2.0 mmol). The reaction mixture was heated to 100° C. for 24 hr, or until no dichloroquinone is present by TLC. To the reaction mixture was added pyrrolidine (20 mmol, 1.67 mL), and the mixture was heated to 100° C. for 4 hr. The reaction mixture was partitioned between ethylacetate and water. The organic phase was separated and washed with water (3×) and brine, and dried over sodium sulfate. Chromatography on silica gel eluted with hexanes/ethylacetate (10:1) gave the title compound as a violet amorphous solid. $^1H$ NMR (DMSO-$d_6$): δ=7.93 (m, 1H), 7.91 (m, 1H), 7.84 (s, 1H), 7.75 (m, 2H), 7.13 (br q, 1H), 6.48–6.36 (m, 3H), 3.48 (m, 4H), 1.61 (m, 4H) ppm.

EXAMPLE 17

2-(N-3-fluoroanilino)-3-dimethylamino-1,4-naphthoquinone (MES 10627)

To a solution of 2,3-dichloro-1,4-naphthoquinone (0.5 mmol) in dry DMSO (1.25 mL) was added 3-fluoroaniline (0.5 mmol) and ethyldi(isopropyl)amine (0.5 mmol). The reaction mixture was heated to 50° C. for 76 hr, or until no dichloroquinone is present by TLC. To a 250 μl aliquot of the reaction mixture was added a solution of dimethylamine in THF (1 mmol of a 2.0M solution, 500 μL), and the mixture was heated to 100° C. for 48 hr. The reaction mixture was partitioned between ethylacetate and water. The organic phase was separated and washed with water (3×) and brine, and dried over sodium sulfate. Chromatography on silica gel eluted with hexanes/ethylacetate (10:1) gave the title compound as a violet amorphous solid. $^1H$ NMR (DMSO-$d_6$): δ=8.13 (s, 1H), 7.94 (m, 2H), 7.76 (m, 2H), 7.17 (q, 1H), 6.73–6.57 (m, 3H), 2.76 (s, 6H)ppm.

EXAMPLE 18

2-(N-4-fluoroanilino)-3-(2-methylpyrrolidino)-1,4-naphthoquinone (MES 10638)

To a solution of 2,3-dichloro-1,4-naphthoquinone (1 mmol) in dry DME (2.5 mL) was added 4-fluoroaniline (1 mmol) and triethylamine (1 mmol). The reaction mixture was heated to 100° C. for 24 hr, or until no dichloroquinone is present by TLC. To the reaction mixture was added 2-methyl-pyrrolidine (2 mmol), and the mixture was heated to 100° C. for 24 hr. The reaction mixture was partitioned between ethylacetate and water. The organic phase was separated and washed with water (3×) and brine, and dried over sodium sulfate. Chromatography on silica gel eluted with hexanes/ethylacetate (10:1) gave the title compound as a purple/blue glassy solid. $^1H$ NMR (DMSO-$d_6$): δ=7.96 (s, 1H), 7.92 (m, 2H), 7.75 (m, 2H), 7.00 (m, 2H), 6.75 (m, 2H), 3.86 (m, 1H), 3.62 (m, 1H), 3.51 (m, 1H), 1.70 (m, 2H), 1.26 (m, 2H), 0.91 (d, 3H) ppm.

EXAMPLE 19

2-(N-4-fluoroanilino)-3-(2-(S)-methoxymethylpyrrolidino)-1,4-naphthoquinone (MES 10639)

To a solution of 2,3-dichloro-1,4-naphthoquinone (0.5 mmol) in dry DME (1 mL) was added 4-fluoroaniline (0.5 mmol) and triethylamine (0.5 mmol). The reaction mixture was heated to 100° C. for 24 hr, or until no dichloroquinone is present by TLC. To the reaction mixture was added 2-((S)-methoxymethyl)-pyrrolidine (2 mmol), and the mixture was heated to 100° C. for 48 hr. The reaction mixture was partitioned between ethylacetate and water. The organic phase was separated and washed with water (3×) and brine, and dried over sodium sulfate. Chromatography on silica gel eluted with hexanes/ethylacetate (10:1) gave the title compound as a blue/grey glassy solid. $^1H$ NMR (DMSO-$d_6$): δ=7.96 (s, 1H), 7.94 (m, 2H), 7.75 (m, 2H), 6.99 (m, 2H), 6.80 (m, 2H), 3.89 (m, 1H), 3.52 (m, 1H), 3.46 (m, 1H), 3.18 (m, 1H), 3.12 (s, 3H), 1.69 (m, 2H), 1.43 (m, 2H) ppm.

EXAMPLE 20

2-(4-(2-furanoylamino)phenylamino)-3-pyrrolidino-1,4-naphthoquinone (MES 13366)

A solution of 2,3-dichloro-1,4-naphthoquinone (5.0 g, 22 mmol, 1 eq), p-phenylenediamine (4.75 g, 44 mmol, 2 eq) in DMF (100 ml) was stirred at room temperature for 2 hours and then mixed with water (1 L). Purple solids were collected by filtration and dried under reduced pressure to give 2-(4-aminophenylamino)-3-dichloro-1,4-naphthoquinone (6.4 g, 21.4 mmol, 98% yield).

To the mixture of 2-furoic acid (1 g, 8.93 mmol, 1 eq) and DMF (1 drop) in $CH_2Cl_2$ (20 ml) was added thionyl chloride (1.6 ml, 22.0 mmol, 2.5 eq) dropwise under nitrogen. After stirring the reaction mixture at room temperature overnight, solvents were removed to give a white solid, which was dried under vacuum.

A solution of the white solid and 2-(4-aminophenylamino)-3-dichloro-1,4-naphthoquinone (200 mg, 0.67 mmol, 1 eq) in DMF (10 ml) was stirred at room temperature for 2 hours. The solution was then partitioned between ethyl acetate (100 ml) and water (100 ml). The organic phase was washed with water (4×100 ml). Removal of the ethyl acetate gave a crude red solid.

The crude solid and pyrrolidine (0.5 ml) in DMF (10 ml) was stirred at 50° C. for 4 hours. The reaction mixture was then partitioned between ethyl acetate (150 ml ) and water (150 ml). The organic phase was washed with water (4×150 ml), brine (150 ml) and dried over $Na_2SO_4$. Removal of the solvent gave a solid, which was passed through a silica gel plug ($SiO_2$, EtOAc/petroleum ether, 1:1) to remove baseline impurities. Evaporation of the solvent under reduced pressure gave a green solid (123 mg, 43% yield). A portion of the product was further purified using flash column chromatography ($SiO_2$, EtOAc/petroleum ether, 1:5, 2 consecutive columns) to obtain a sample of high purity. $^1H$ NMR (DMSO-$d_6$): 9.98 (s, 1H), 7.92 (m, 3H), 7.76 (m, 3H), 7.54 (d, 2H,), 7.25 (d, 1H), 6.68 (m, 3H), 4.05–3.95 (m, 1H), 3.44 (m, 4H), 1.58 (m, 4H) ppm.

EXAMPLE 21

N-4-((3-pyrrolidino-1,4-naphthalenedion-2-yl)amino)phenyl-O-(1-methylethyl)carbamate (MES 13372)

To a solution of 2-propanol (0.462 ml, 6 mmol, 1 eq) in anhydrous THF (25 ml) was added carbonyldiimidazole (1.23 g, 7.5 mmol, 1.25 eq) at RT. The reaction mixture was then stirred for 2 hours. To the above reaction mixture, a solution of p-phenylenediamine (648 mg, 6 mmol, 1 eq) and DMAP (0.12 g, 1 mmol) in anhydrous acetonitrile (25 ml) was then added. The reaction mixture was heated at reflux for 8 hours and then cooled to room temperature. Concentration in vacuum and silica gel column chromatography purification ($SiO_2$, 50% EtOAc/petroleum ether) gave a bright yellow oil.

A solution of the above oil and triethylamine (0.54 ml) in DMF (5 ml), was added 2,3-dichloro-1,4-naphthoquinone (681 mg, 3 mmol, 1 eq) at 0° C., then stirred at 50° C. for 6 hours. After this time, the reaction mixture was partitioned between ethyl acetate (100 ml) and water (100 ml). The organic phase was washed with water (4×100 ml) and then brine (100 ml). Removal of the ethyl acetate gave a crude red solid.

The crude solid and pyrrolidine (5 ml, 60 mmol, 20 eq) in DMSO (5 ml) was stirred at 50° C. for 5 hours. After this time, the reaction mixture was partitioned between ethyl acetate (100 ml) and water (100 ml). The organic phase was washed with water (4×100 ml), brine (100 ml) and dried over $Na_2SO_4$. Removal of the solvent gave a solid, which was passed through a silica gel plug ($SiO_2$, EtOAc/petroleum ether, 1:1) to remove baseline impurities. Evaporation of the solvent under reduced pressure gave a green solid (866 mg, 67% yield). A portion of the product was further purified using flash column chromatography ($SiO_2$, EtOAc/petroleum ether, 1:1, 3 consecutive columns) to obtain a sample of high purity. $^1H$ NMR (DMSO-$d_6$): 9.35 (br s, 1H), 7.92 (m, 2H), 7.76 (m, 2H), 7.63 (s, 1H,), 7.22 (d, 2H), 6.63 (d, 2H), 4.85 (hp, 1H), 3.40 (m, 4H), 1.56 (m, 4H), 1.24 (d, 6H) ppm.

EXAMPLE 22

N-4-((3-pyrrolidino-1,4-naphthalenedion-2-yl)amino)phenyl-O-methylcarbamate (MES 13374)

A solution of 2,3-dichloro-1,4-naphthoquinone (5.0 g, 22 mmol,), p-phenylenediamine (4.75 g, 44 mmol,) in DMF (100 ml) was stirred at room temperature for 2 hours and then mixed with water (1 L). Purple solids were collected by filtration and dried under reduced pressure to give 2-(4-aminophenylamino)-3-dichloro-1,4-naphthoquinone (6.4 g, 21.4 mmol, 98% yield).

To a solution of 2-(4-aminophenylamino)-3-dichloro-1,4-naphthoquinone (500 mg, 1.68 mmol, 1 eq) and triethylamine (0.54 ml) in DMF (5 ml) was added methyl chloroformate (0.3 ml, 1.68 mmol, 1 eq) at 0° C. The reaction was stirred at RT for one hour and then partitioned between ethyl acetate (100 ml) and water (100 ml). The organic phase was washed with water (4×100 ml), brine (100 ml). Removal of the ethyl acetate gave a crude red solid.

The crude solid and pyrrolidine (2.8 ml, 33.8 mmol, 20 eq) in DMSO (5 ml) were stirred at 50° C. for 5 hours. The reaction mixture was partitioned between ethyl acetate (100 ml) and water (100 ml). The organic phase was washed with water 4 times, brine and dried over $Na_2SO_4$. Removal of the solvent gave a solid, which was passed through a silica gel plug ($SiO_2$, EtOAc/petroleum ether, 1:1) to remove baseline impurities. Evaporation of the solvent under reduced pressure gave a green solid (400 mg, 60% yield). A portion of the product was further purified using flash column chromatography ($SiO_2$, EtOAc/petroleum ether, 1:1, 3 consecutive columns) to obtain a sample of good purity (83% pure). $^1H$ NMR (DMSO-$d_6$): 9.38 (br s, 1H), 7.92 (m, 2H), 7.76 (m, 2H), 7.64 (s, 1H,), 7.21 (d, 2H), 6.62 (d, 2H), 3.61 (s, 3H), 3.40 (m, 4H), 1.56 (m, 4H) ppm.

EXAMPLE 23

N-3-((3-pyrrolidino-1,4-naphthalenedion-2-yl)amino)phenyl-O-methylcarbamate (MES 13375)

To a solution of o-phenylenediamine (4.75 g, 44 mmol) in DMF (100 ml) was added 2,3-dichloro-1,4-naphthoquinone (5.0 g, 22 mmol). After the solution was then stirred at room temperature for 8 hours, it was mixed with water (1 L). Red brown solid materials were collected by filtration and dried. under reduced pressure to give 2-(3-aminophenylamino)-3-dichloro-1,4-naphthoquinone (6.1 g, 20.3 mmol, 92% yield).

To a solution of 2-(3-aminophenylamino)-3-dichloro-1,4-naphthoquinone (500 mg, 1.68 mmol) and triethylamine (0.54 ml) in DMF (5 ml) was added methyl chloroformate (0.3 ml, 1.68 mmol) at 0° C. The reaction was stirred at RT for one hour and then partitioned between ethyl acetate and water. The organic phase was washed with water four times, followed by washing with brine. Removal of the ethyl acetate gave a crude red solid.

The crude solid and pyrrolidine (2.8 ml, 33.8 mmol) in DMSO (5 ml) was stirred at 50° C. for 5 hours. The reaction mixture was partitioned between ethyl acetate and water. The organic phase was washed with water 4 times, brine and dried over $Na_2SO_4$. Removal of the solvent gave a solid, which was passed through a silica gel plug ($SiO_2$, EtOAc/petroleum ether, 1:1) to remove baseline impurities. Evaporation of the solvent under reduced pressure gave a blue-green solid (387 mg, 58% yield). A portion of the product was further purified using flash column chromatography ($SiO_2$, EtOAc/petroleum ether, 1:1, 3 consecutive columns) to obtain a sample of high purity. $^1H$ NMR (DMSO-$d_6$): 9.47 (br s, 1H), 7.94 (m, 2H), 7.77 (m, 2H), 7.60 (s, 1H,), 7.02 (dd, 1H), 6.86 (dd, 1H), 6.68 (s, 1H), 6.49 (dd, 1H), 3.62 (s, 3H), 3.52 (m, 4H), 1.53 (m, 4H) ppm.

EXAMPLE 24

$N^1$-4-((3-pyrrolidino-1,4-naphthalenedion-2-yl)amino)phenyl-$N^2$-(1-methylethyl)urea (MES 13378)

The title compound was produced similarly to Example 11 by treatment of Example 7 with isopropyl isocyanate.

HPLC purification of the crude product (½ of the total) gave MES 13378 (40.7 mg). $^1$H NMR (CDCl$_3$): 8.06–7.78 (m, 2H), 7.70–7.59 (m, 2H), 7.09 (d, 2H, J=9.0 Hz), 6.60 (d, 2H, J=9.0 Hz), 4.05–3.95 (m, 1H), 3.58–3.48 (m, 4H), 1.72–1.63 (m, 4H), 1.14 (d, 6H, J=6.3) ppm.

EXAMPLE 25

N$^1$-4-((3-pyrrolidino-1,4-naphthalenedion-2-yl)amino)phenyl-N$^2$-phenylurea (MES 13380)

To a solution of p-phenylenediamine (2.67 g, 2.5 mmol) in 120 ml dichloromethane, was added phenyl isocyanate (2.6 ml, 2.5 mmol). The reaction mixture was stirred for 2 hours at RT to give a white solid, which was filtrated and dried under vacuum. To the solution of this white solid (500 mg, 2.2 mmol) and triethylamine (0.34 ml) in DMSO (5 ml) was added 2,3-dichloro-1,4-naphthoquinone (500 mg, 2.2 mmol) at RT, and the reaction mixture was stirred at 50° C. for 3 hours. After this time, the reaction mixture was partitioned between ethyl acetate (100 ml) and water (100 ml). The organic phase was washed with water (4×100 ml), followed by washing with brine (100 ml). Removal of the ethyl acetate gave a dark purple solid.

The crude solid and pyrrolidine (0.2 ml, 2.4 mmol) in DMSO (5 ml) was stirred at 50° C. for 5 hours. After this time, the reaction mixture was partitioned between ethyl acetate (50 ml) and water (50 ml). The organic phase was washed with water (4×50 ml), brine (50 ml) and dried over Na$_2$SO$_4$. Removal of the solvent gave a solid, which was passed through a silica gel plug (SiO$_2$, EtOAc/petroleum ether, 3:2) to remove baseline impurities. Evaporation of the solvent under reduced pressure gave a green solid (76 mg, 8% overall yield). A portion of the product was further purified using flash column chromatography (SiO$_2$, EtOAc/petroleum ether, 3:2, 2 consecutive columns) to obtain a sample of high purity. $^1$H NMR (DMSO-d$_6$): 8.57 (s, 1H), 8.39 (s, 1H), 7.92 (m, 2H), 7.75 (m, 2H), 7.67 (s, 1H,), 7.41 (d, 2H), 7.26 (m, 4H), 6.83 (dd, 1H), 6.63 (d, 2H), 3.41 (m, 4H), 1.57 (m, 4H) ppm.

EXAMPLE 26

N$^1$-4-((3-pyrrolidino-1,4-naphthalenedion-2-yl)amino)phenyl-N$^2$-methylurea (MES 13382)

Example 10 (0.3 mmol, 100 mg) was stirred in CH$_2$Cl$_2$ (5 mL) in an ice-bath. A solution of 1,1'-carbonyldiimidazole (0.40 mmol, 65 mg) in 1 mL of CH$_2$Cl$_2$ was added. The solution was stirred at rt for 1 hr. Methylamine (1 mL, 2M in THF) was added. The solution was stirred at rt for 1 hr and concentrated to give a purple solid (135 mg). HPLC purification gave 88.1 mg of the title compound. $^1$H NMR (DMSO-d$_6$): 8.21 (s, 1H), 7.90 (m, 2H), 7.74 (m, 2H), 7.63 (s, 1H,), 7.18 (d, 2H), 6.61 (d, 2H), 5.83 (m 1H), 3.40 (m, 4H), 2.61 (d, 3H), 1.54 (m, 4H) ppm.

EXAMPLE 27

N$^1$-4-((3-pyrrolidino-1,4-naphthalenedion-2-yl)amino)phenyl-N$^2$-(2-methoxyethyl)urea (MES 13384)

Following the procedures for the preparation of Example 26, Example 7 was reacted with carbonyldiimidazole followed by the treatment with 2-methoxyethylamine to produce the title compound (78 mg). $^1$H NMR (CDCl$_3$): 8.10–7.92 (m, 2H), 7.70–7.59 (m, 2H), 7.06 (d, 2H, J=9.0 Hz), 6.60 (d, 2H, J=9.0 Hz), 3.60–3.40 (m, 8H), 3.37 (s, 3H), 1.80–1.62 (m, 4H) ppm.

EXAMPLE 28

2-(N-(4-carbamidoanilino))-3-pyrrolidino-1,4-naphthoquinone (MES 10570)

The title compound was prepared employing the same procedure as for the preparation of Example 10, 2,3-dichloro-1,4-naphthoquinone reacted with 4-aminobenzamide followed by treatment with pyrrolidine to give the title compound as a dark purple solid (28.2 mg). $^1$H NMR (CD$_3$OD): 8.06–7.98 (m, 2H), 7.74–7.65 (m, 2H), 7.75 (d, 2H, J=9.5 Hz), 6.61 (d, 2H, J=9.5 Hz), 3.68–3.59 (m, 4H), 1.79–1.69 (m, 4H) ppm.

EXAMPLE 29

2-(N-3,4-difluoroanilino)-3-pyrrolidino-1,4-naphthoquinone (MES 68764)

The title compound was prepared employing the method described for Example 16 substituting 3,4-difluoroaniline (2.0 mmol) for 3-fluoroaniline. $^1$H NMR δ=7.91 (m, 2H), 7.84 (s, 1H), 7.74 (m, 2H), 7.18 (m, 1H), 6.63 (m, 1H), 6.45 (m, 1 H), 3.46 (m, 2H), 1.62 (m, 2H) ppm. The compound may also be purchased from ChemBridge Corp. (San Diego, Calif., cat #6574537).

EXAMPLE 30

2-(N-4-Fluoroanilino)-3-pyrrolidino-1,4-naphthoquinone (MES 68769)

The title compound was prepared employing the method described for Example 16 substituting 4-fluoroaniline (2.0 mmol) for 3-fluoroaniline. $^1$H NMR δ=7.92 (m, 2H), 7.73 (m, 2H), 7.71 (s, 1H), 6.98 (m, 2H), 6.69 (m, 2H), 3.41 (m, 4H), 1.55 (m, 4H) ppm. This compound may also be purchased from Specs/Biospecs (Rijswijk, The Netherlands, cat #AO-567/14978002).

EXAMPLE 31

Toxicity of Compounds of the Invention 6D-2 cells (MCF-7 human breast cancer cells stably transfected with luciferase linked to the 5' and 3' UTRs of human HER2) were added to 96-well plates at 7500 cells per well in 200 μL medium and incubated for 24 hours at 100% humidity, 5% CO$_2$, and 37° C. Compounds were diluted from DMSO stock solutions into medium and were added at various concentrations. The 6D-2 cells were incubated for 16 hours at which time the volume of medium in each well was reduced to 100 μL using a plate washer. 20 μL of MTS cell viability reagent (Promega, Madison, Wis.) was then added to each well, and the plates were incubated for 1–4 hours. A plate containing wells with 100 μL medium plus MTS reagent was prepared to determine the background reading. The plates were read on the Wallac 2 plate reader (PerkinElmer Life Science, Boston, Mass.) at 490 nm. Percent viability was calculated as (O.D. of compound treated cells—background O.D.)/(O.D. of DMSO treated cells—background O.D.)×100. MT-4 cells (adult human T-cell leukemia cells) were plated at 1.5×10$^5$ cells per well in 200 μL medium and incubated for at least one hour before the addition of compounds. The cells were incubated for 5 days at 100% humidity, 5% CO$_2$, and 37° C. Cell viability was determined as described for 6D-2 cells.

Compounds of the invention containing a pyrrolidine substituent were tested for toxicity to cancerous and non-cancerous cells. 6D-2 cellular activity is representative of potency as an antitumor agent. MT-4 cellular activity is representative of general toxicity. The results are shown in Table 1. A high IC50 for MT-4 cells and a low IC50 for 6D-2 cells is indicative of a compound of potential therapeutic use in treating or preventing proliferative diseases, such as cancer.

TABLE 1

Cellular toxicity of Representative compounds

| Example # | MES # | 6D-2 24 hr (IC50) | MT-4 5 day (IC50) |
|---|---|---|---|
| Example 3A | 10555 | 0.37 | 5.16 |
| Example 3B | 10556 | 4.08 | 6.79 |
| Example 4 | 10557 | 1.48 | 2.51 |
| Example 5 | 10563 | 0.77 | 6.69 |
| Example 6 | 10553 | 0.57 | 2.78 |
| Example 7 | 10554 | 0.07 | 0.16 |
| Example 8 | 10559 | 0.12 | 1.11 |
| Example 9 | 10564 | 0.1 | 0.52 |
| Example 10 | 10567 | 6.78 | 1.18 |
| Example 11 | 10571 | 0.33 | 6.15 |
| Example 12 | 10572 | 0.1 | 8.7 |
| Example 13 | 10619 | 70% @ 10 mM | 80% @ 10 mM |
| Example 14 | 10620 | 0.76 | 2.1 |
| Example 15 | 10622 | 60% @ 10 mM | 1 |
| Example 16 | 10626 | 1.36 | 68% @ 10 mM |
| Example 17 | 10627 | 10 | 100% @ 10 mM |
| Example 18 | 10638 | 2.63 | 5.24 |
| Example 19 | 10639 | 8.95 | 97% @ 10 mM |
| Example 20 | 13366 | 0.06 | 0.11 |
| Example 21 | 13372 | 1.38 | 2 |
| Example 22 | 13374 | 0.14 | 0.47 |
| Example 23 | 13375 | 0.87 | 10.2 |
| Example 24 | 13378 | 0.18 | 1.68 |
| Example 25 | 13380 | 1.06 | 2.22 |

TABLE 1-continued

Cellular toxicity of Representative compounds

| Example # | MES # | 6D-2 24 hr (IC50) | MT-4 5 day (IC50) |
|---|---|---|---|
| Example 26 | 13382 | 0.11 | 0.75 |
| Example 27 | 13384 | 0.21 | 0.56 |
| Example 28 | 10570 | 0.31 | 56% @ 10 mM |
| Example 29 | 68764 | 2.34 | 40% @ 10 mM |
| Example 30 | 68769 | 0.52 | 4.47 |
| Example 2 | 51151 | 0.25 | 0.08 |

Other Embodiments

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention.

All publications, patents, and patent applications mentioned in this specification are herein incorporated by reference to the same extent as if each individual publication, patent, or patent application was specifically and individually to be incorporated by reference.

Other embodiments are within the claims.

What is claimed is:

1. A compound having the formula:

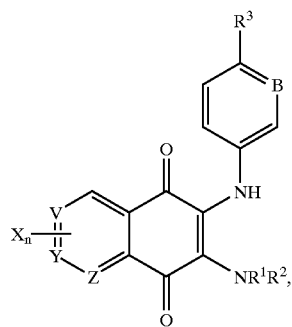

or a pharmaceutically acceptable salt thereof, where V, Y, and Z are independently N, CH, or C; B is N, CH, or $CR^4$, where $R^4$ is F or lower alkyl; X is independently H, Hal, lower alkyl, $OR^5$, $SR^6$, or $NR^7R^8$, where $R^5$, $R^6$, $R^7$, and $R^8$ are independently H or lower alkyl, and n is 1, 2, 3, or 4; $R^1$ and $R^2$ together are $(CR^9R^{10})_m$, where $R^9$ and $R^{10}$ are independently H, lower alkyl, $CH_2OR^{11}$, $(CH_2)_oNR^{12}R^{13}$, or $OR^{14}$, where $R^{11}$, $R^{12}$, $R^{13}$, and $R^{14}$ are independently H, lower alkyl, aryl, or alkaryl, m is 2, 3, 4, or 5, and o is 0 or 1; and $R^3$ is H, lower alkyl, F, $OR^{15}$, where $R^{15}$ is H, lower alkyl, or aralkyl, or a substituent of the structure:

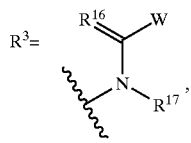

where $R^{16}$ is NH, O, or S; $R^{17}$ is H, lower alkyl, or aralkyl; and W is lower alkyl, lower alkenyl, lower alkynyl, aryl, heteroaryl, alkaryl, $OR^{18}$, or $NR^{19}R^{20}$, where $R^{18}$, $R^{19}$, and $R^{20}$ are independently H, lower alkyl, lower alkenyl, lower alkynyl, aryl, alkaryl, aralkyl, or $(CH_2)_kCH_2OR^{21}$, where $R^{21}$ is H or lower alkyl, and k is 1,2, 3, or 4, provided that when $X_n$ is H, V, Y, and Z are C or CH, $R^1$ and $R^2$ together are $(CH_2)_4$, B is $CR^4$, and $R^4$ is F, $R^3$ is not F or H; when $X_n$ is H, V, Y, and Z are C or CH, $R^1$ and $R^2$ together are $(CH_2)_4$, B is $CR^4$, and $R^4$ is Me, $R^3$ is not H; when $X_n$ is H, V, Y, and Z are C or CH, $R^1$ and $R^2$ together are $(CH_2)_4$, B is $CR^4$, and $R^4$ is H, $R^3$ is not H or F; when $X_n$ is H, V, Y, and Z are C or CH, $R^1$ and $R^2$ together are $(CH_2)_4$, B is CH, W is methyl, and $R^{16}$ is O, $R^{17}$ is not H; when $X_n$ is H, V, Y, and Z are C or CH, B is CH, and $R^1$ and $R^2$ together are $(CH_2)_5$, $R^3$ is not methoxy; when $X_n$ is H, V, Y, and Z are C or CH, B is CH, and $R^1$ and $R^2$ together are $(CH_2)_5$, $R^3$ is not F; and $X_n$ is H, V, Y, and Z are C or CH, B is CH, and $R^1$ and $R^2$ together are $(CH_2)_5$, $R^3$ is not ethoxy.

2. The compound of claim 1 having the formula:

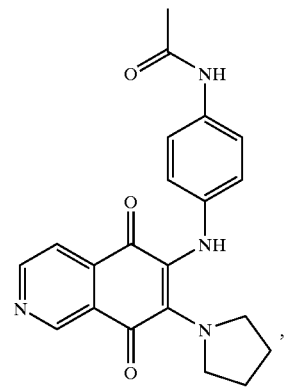

or a pharmaceutically acceptable salt thereof.

3. The compound of claim 1 having the formula:

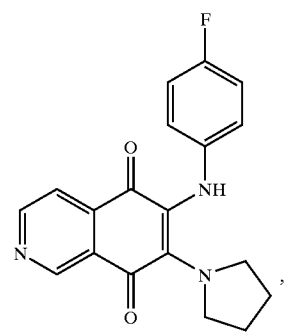

or a pharmaceutically acceptable salt thereof.

4. The compound of claim 1 having the formula:

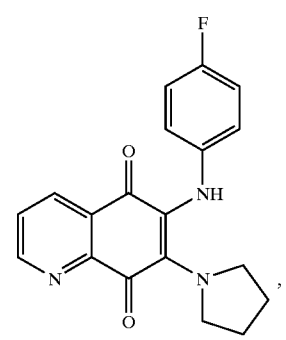

or a pharmaceutically acceptable salt thereof.

5. The compound of claim 1, wherein at least one of B, V, Y, and Z is N, or a pharmaceutically acceptable salt thereof.

6. The compound of claim 1 having the formula:

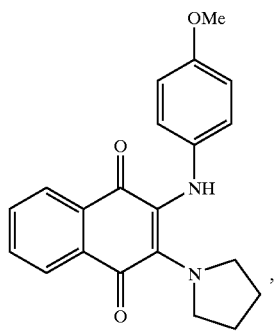

or a pharmaceutically acceptable salt thereof.

7. The compound of claim 1 having the formula:

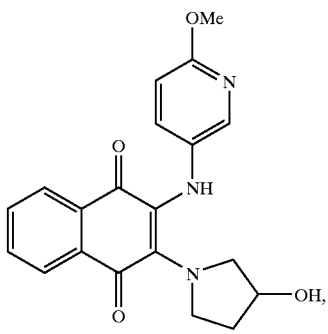

or a pharmaceutically acceptable salt thereof.

8. The compound of claim 1 having the formula:

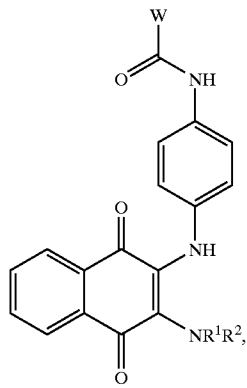

or a pharmaceutically acceptable salt thereof.

9. The compound of claim 1 having the formula:

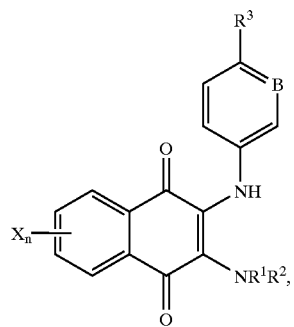

or a pharmaceutically acceptable salt thereof.

10. The compound of claim 1 having the formula:

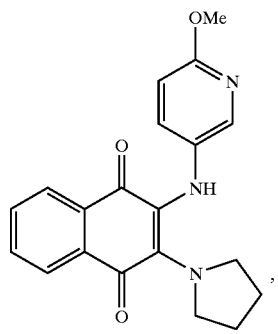

or a pharmaceutically acceptable salt thereof.

11. A compound having the formula:

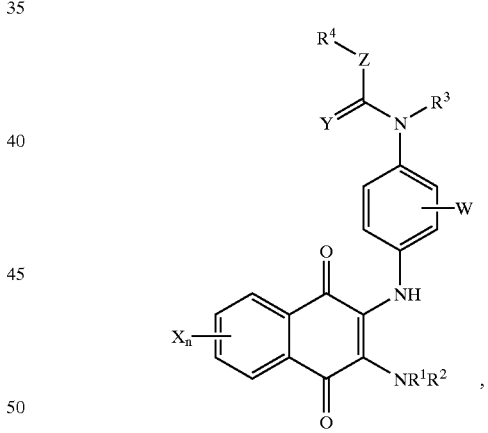

or a pharmaceutically acceptable salt thereof, where W is H, lower alkyl, aryl, Hal, or $OR^5$, where $R^5$ is H or lower alkyl; X is independently H, Hal, lower alkyl, $OR^6$, $SR^7$, or $NR^8R^9$, where $R^6$, $R^7$, $R^8$, and $R^9$ are independently H or lower alkyl, and n is 1, 2, 3, or 4; Y is NH, O, or S; Z is O or $NR^{10}$, where $R^{10}$ is H, lower alkyl, or lower alkenyl; $R^1$ and $R^2$ are independently H, Me, or Et, or $R^1$ and $R^2$ together are $(CR^{11}R^{12})_m$, where $R^{11}$ and $R^{12}$ are independently H, lower alkyl, $CH_2OR^{13}$, $(CH_2)_oNR^{14}R^{15}$, or $OR^{16}$, where $R^{13}$, $R^{14}$, $R^{15}$, and $R^{16}$ are H, lower alkyl, aryl, or alkaryl, m is 2, 3, 4, or 5, and o is 0 or 1; $R^3$ is H or lower alkyl; and $R^4$ is H, lower alkyl, lower alkenyl, lower alkynyl, aryl, alkaryl, or $(CH_2)_kCH_2OR^{17}$, where $R^{17}$ is H or lower alkyl, and k is 1, 2, 3, or 4.

12. The compound of claim 11, wherein W is H, or a pharmaceutically acceptable salt thereof.

13. The compound of claim 12 having the formula:

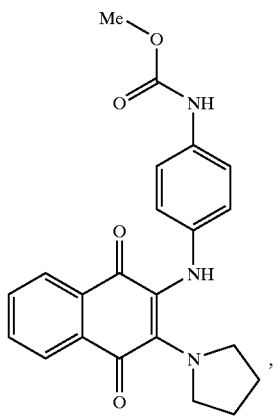

or a pharmaceutically acceptable salt thereof.

14. The compound of claim 12 having the formula:

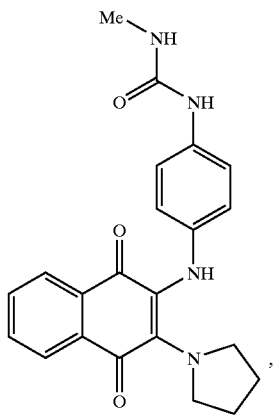

or a pharmaceutically acceptable salt thereof.

15. The compound of claim 12 having the formula:

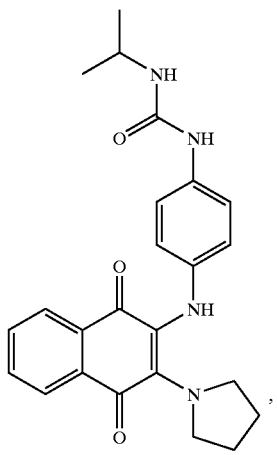

or a pharmaceutically acceptable salt thereof.

16. The compound of claim 12 having the formula:

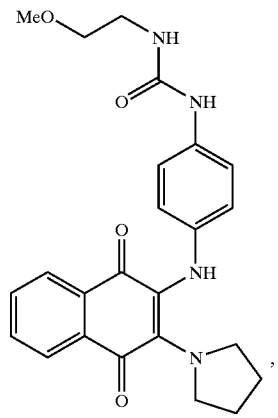

or a pharmaceutically acceptable salt thereof.

17. The compound of claim 12 having the formula:

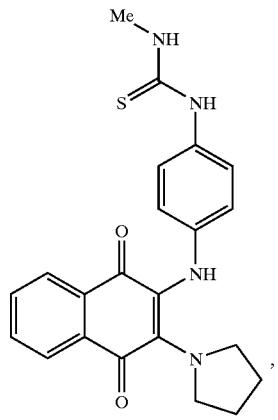

or a pharmaceutically acceptable salt thereof.

18. The compound of claim 12 having the formula:

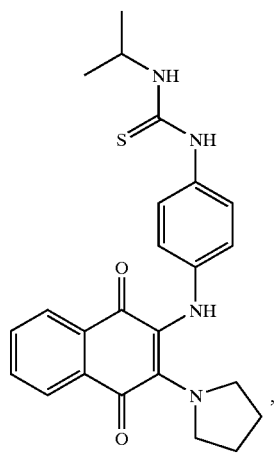

or a pharmaceutically acceptable salt thereof.

19. A compound having the formula:

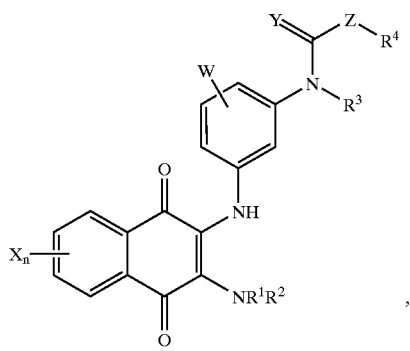

or a pharmaceutically acceptable salt thereof, where W is H, lower alkyl, aryl, Hal, or $OR^5$, where $R^5$ is H or lower alkyl; X is independently H, Hal, lower alkyl, $OR^6$, $SR^7$, or $NR^8R^9$, where $R^6$, $R^7$, $R^8$, and $R^9$ are independently H or lower alkyl, and n is 1, 2, 3, or 4; Y is NH, O or S; Z is O or $NR^{10}$, where $R^{10}$ is H, lower alkyl, or lower alkenyl; $R^1$ and $R^2$ are independently H, Me, or Et, or $R^1$ and $R^2$ together are $(CR^{11}R^{12})_m$, where $R^{11}$ and $R^{12}$ are independently H, lower alkyl, $CH_2OR^{13}$, $(CH_2)_oNR^{14}R^{15}$, or $OR^{16}$, where $R^{13}$, $R^{14}$, $R^{15}$, and $R^{16}$ are H, lower alkyl, aryl, or alkaryl, m is 2, 3, 4, or 5, and o is 0 or 1; $R^3$ is H or lower alkyl; and $R^4$ is H, lower alkyl, lower alkenyl, lower alkynyl, aryl, alkaryl, or $(CH_2)_kCH_2OR^{17}$, where $R^{17}$ is H or lower alkyl, and k is 1, 2, 3, or 4.

20. The compound of claim 19 having the formula:

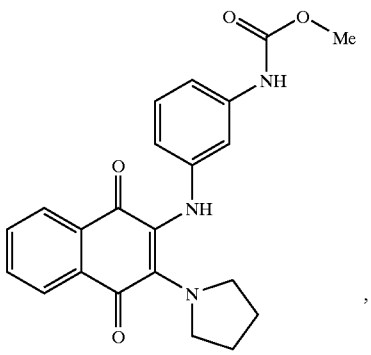

or a pharmaceutically acceptable salt thereof.

21. A compound having the formula:

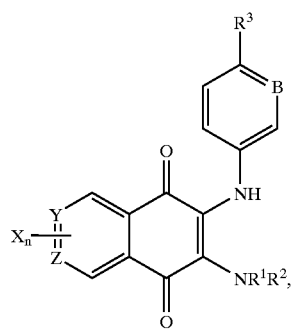

or a pharmaceutically acceptable salt thereof, where Y and Z are independently C, CH, or N; B is N or $CR^4$, where $R^4$ is F, lower alkyl, or H; X is independently H, Hal, lower alkyl, $OR^5$, $SR^6$, or $NR^7R^8$, where $R^5$, $R^6$, $R^7$, and $R^8$ are independently H or lower alkyl, and n is 1, 2, 3, or 4; $R^1$ and $R^2$ are independently H, Me, or Et, or $R^1$ and $R^2$ together are $(CR^9R^{10})_m$, where $R^9$ and $R^{10}$ are independently H, lower alkyl, $CH_2OR^{11}$, $(CH_2)_oNR^{12}R^{13}$, or $OR^{14}$, where $R^{11}$, $R^{12}$, $R^{13}$, and $R^{14}$ are H, lower alkyl, aryl, or alkaryl, m is 2, 3, 4, or 5, and o is 0 or 1; $R^3$ is a substituent of the structure:

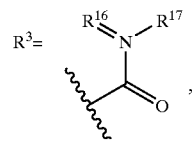

where $R^{16}$ and $R^{17}$ are independently H, lower alkyl, aryl, or aryl.

22. The compound of claim 21 having the formula:

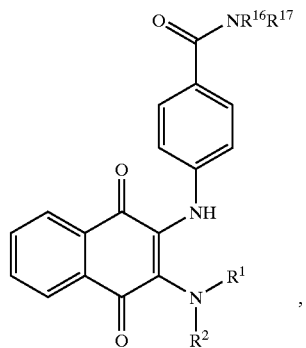

or a pharmaceutically acceptable salt thereof.

23. The compound of claim 21 having the formula:

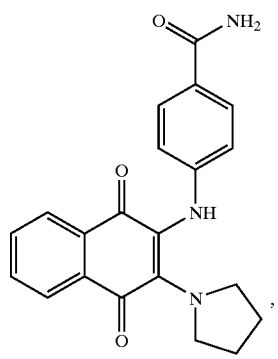

or a pharmaceutically acceptable salt thereof.

24. A compound having the formula:

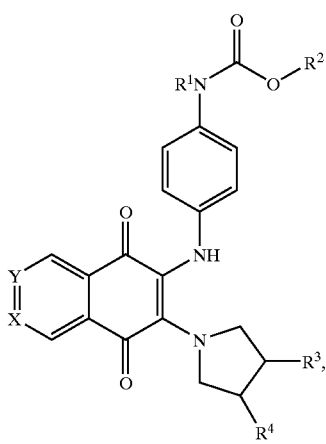

or a pharmaceutically acceptable salt thereof, where X and Y are independently N or CH; $R^1$ is H, lower alkyl or aralkyl; $R^2$ is lower alkyl, or aralkyl; $R^3$ and $R^4$ are independently H or $OR^5$, where $R^5$ is H, lower alkyl, or $NR^6R^7$, where $R^6$ and $R^7$ are independently H or lower alkyl.

25. The compound of claim 24 having the formula:

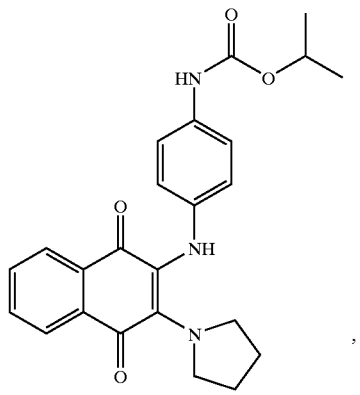

or a pharmaceutically acceptable salt thereof.

26. The compound of claim 24 having the formula:

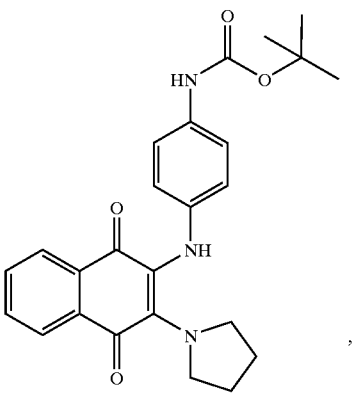

or a pharmaceutically acceptable salt thereof.

27. A compound having the formula:

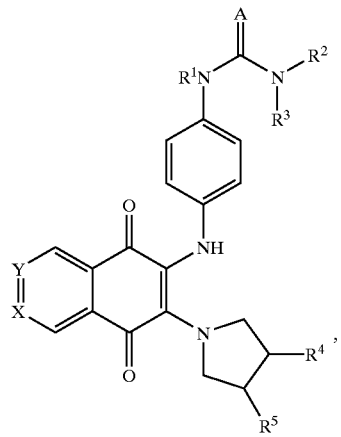

or a pharmaceutically acceptable salt thereof, where X and Y are independently N or CH; A is O or S; $R^1$ is H, lower alkyl, or aralkyl; $R^2$ and $R^3$ are independently lower alkyl or aralkyl; and $R^4$ and $R^5$ are independently H or $OR^6$, where $R^6$ is H, lower alkyl, or $NR^7R^8$, where $R^7$ and $R^8$ are independently H or lower alkyl.

28. The compound of claim 1, wherein m is 4.
29. The compound of claim 11, wherein $R^1$ and $R^2$ together are $(CR^{11}R^{12})_m$.
30. The compound of claim 29, wherein m is 4.
31. The compound of claim 19, wherein $R^1$ and $R^2$ together are $(CR^{11}R^{12})_m$.
32. The compound of claim 31, wherein m is 4.
33. The compound of claim 21, wherein $R^1$ and $R^2$ together are $(CR^{11}R^{12})_m$.
34. The compound of claim 33, wherein m is 4.

* * * * *